United States Patent
Shukla et al.

(10) Patent No.: US 10,370,515 B2
(45) Date of Patent: *Aug. 6, 2019

(54) SILVER-CONTAINING NON-AQUEOUS COMPOSITION CONTAINING CELLULOSIC POLYMERS

(71) Applicant: Eastman Kodak Company, Rochester, NY (US)

(72) Inventors: Deepak Shukla, Webster, NY (US); Kevin M. Donovan, Bergen, NY (US)

(73) Assignee: EASTMAN KODAK COMPANY, Rochester, NY (US)

( * ) Notice: Subject to any disclaimer, the term of this patent is extended or adjusted under 35 U.S.C. 154(b) by 72 days.

This patent is subject to a terminal disclaimer.

(21) Appl. No.: 15/713,773

(22) Filed: Sep. 25, 2017

(65) Prior Publication Data

US 2019/0092923 A1 Mar. 28, 2019

(51) Int. Cl.

| | | |
|---|---|---|
| *B22F 9/00* | (2006.01) | |
| *C08K 5/098* | (2006.01) | |
| *C08B 3/00* | (2006.01) | |
| *C08B 11/04* | (2006.01) | |
| *C01G 5/00* | (2006.01) | |
| *C08K 3/08* | (2006.01) | |
| *C07F 1/10* | (2006.01) | |

(52) U.S. Cl.
CPC .............. *C08K 5/098* (2013.01); *C08B 3/00* (2013.01); *C08B 11/04* (2013.01); *C01G 5/00* (2013.01); *C07F 1/10* (2013.01); *C08K 2003/0806* (2013.01)

(58) Field of Classification Search
CPC .................................................. B22F 1/0022
See application file for complete search history.

(56) References Cited

U.S. PATENT DOCUMENTS

| | | |
|---|---|---|
| 6,572,673 B2 | 6/2003 | Lee et al. |
| 6,645,444 B2 | 11/2003 | Goldstein |
| 7,329,301 B2 | 2/2008 | Chang et al. |
| 7,892,317 B2 | 2/2011 | Rahman Nia |
| 9,005,663 B2 | 4/2015 | Raghuraman et al. |
| 9,496,068 B2 | 11/2016 | Kurihara et al. |
| 2010/0040865 A1 | 2/2010 | Li |
| 2012/0225126 A1 | 9/2012 | Geckeler et al. |
| 2014/0312284 A1 | 10/2014 | Liu et al. |
| 2015/0004325 A1 | 1/2015 | Walker et al. |
| 2018/0193913 A1* | 7/2018 | Iwai ........................ B22F 1/00 |

FOREIGN PATENT DOCUMENTS

| | | |
|---|---|---|
| CN | 104263082 B | 5/2017 |
| WO | WO2017033911 A1 | 3/2017 |

OTHER PUBLICATIONS

Chen-Ni Chen et al., "Solution-based [beta]-diketonate silver ink for direct printing of highly conductive features on a flexible substrate," Journal of Materials Chemistry C, vol. 1, No. 33, Jun. 26, 2013, p. 5161, XP055526004, UK.

* cited by examiner

*Primary Examiner* — Kuo Liang Peng
(74) *Attorney, Agent, or Firm* — J. Lanny Tucker

(57) ABSTRACT

A non-aqueous silver precursor composition is composed of (a) one or more cellulosic polymers; (b) reducible silver ions that are present at a weight ratio to the one or more cellulosic polymers of 5:1 to 50:1; (c) an organic solvent that has a boiling point at atmospheric pressure of at least 100° C. and up to but less than 500° C.; and (d) a nitrogenous base having a pKa in acetonitrile of at least 15 and up to and including 25 at 25° C. The Hansen parameter ($\delta_T^{Polymer}$) of each cellulosic polymer is less than or equal to the Hansen parameter ($\delta_T^{Solvent}$) each organic solvent. In addition, the (d) nitrogenous base is present in an equimolar amount or molar excess in relation to the amount of (b) reducible silver ions.

7 Claims, 4 Drawing Sheets

SILVER-CONTAINING NON-AQUEOUS COMPOSITION CONTAINING CELLULOSIC POLYMERS

CROSS-REFERENCE TO RELATED APPLICATIONS

Reference is made to the following commonly assigned and copending patent application, the disclosures of all of which are incorporated herein by reference:

U.S. Ser. No. 15/456,686 filed Mar. 13, 2017 by Shukla and Donovan;

U.S. Ser. No. 15/456,827 filed Mar. 13, 2017 by Shukla, Donovan, and Gillmor;

U.S. Ser. No. 15/456,868 filed Mar. 13, 2017 by Shukla and Donovan;

U.S. Ser. No. 15/713,777, filed on Sep. 25, 2017, by Shukla, Donovan, and Klubek;

U.S. Ser. No. 15/713,786, filed on Sep. 25, 2017, by Shukla and Donovan Base," recently allowed; and U.S. Ser. No. 15/713,795, filed on Sep. 25, 2017, by Shukla and Donovan.

FIELD OF THE INVENTION

This invention relates to a non-aqueous silver precursor composition and a non-aqueous dispersion. The non-aqueous silver precursor composition includes reducible silver ions, a cellulosic polymer, and a nitrogenous base, all in a hydroxylic organic solvent. The non-aqueous dispersion is derived from the non-aqueous silver precursor composition upon reduction of the reducible silver ions, which is facilitated by the presence of the nitrogenous base.

BACKGROUND OF THE INVENTION

It is well known that silver has desirable electrical and thermal conductivity, catalytic properties, and antimicrobial behavior. Thus, silver and silver-containing compounds have been widely used in alloys, metal plating processes, electronic devices, imaging sciences, medicine, clothing or other fibrous materials, and other commercial and industrial articles and processes to take advantage of silver's beneficial properties.

For example, silver compounds or silver metal have been described for use as metallic patterns or electrodes in metal wiring patterns, printed circuit boards (PCB's), flexible printed circuit boards (FPC's), antennas for radio frequency identification (RFID) tags, plasma display panels (PDP's), liquid crystal displays (LCD's), organic light emitting diodes (OLED's), flexible displays, and organic thin film transistors (OTFT's), among other electronic devices known in the art.

Rapid advances are also occurring for making and using various electronic devices for communication, financial, and archival purposes.

Silver is an ideal conductor having electrical conductivity 50 to 100 times greater than indium tin oxide that is commonly used today in many devices. For example, the art has described the preparation of electrically-conductive films by forming and developing (reducing) a silver halide image in "photographic" silver halide emulsions through an appropriate mask to form electrically-conductive grid networks having silver wires having average sizes (width and height) of less than 10 µm and having appropriate lengths.

While silver as an electrical conductor has a wide range of potential uses in the field of printed electronics, the microfabrication of electrically-conductive tracks (grids, wires, or patterns) by photolithographic and electroless techniques is time consuming and expensive, and there is an industrial need for direct digital printing to simplify the processes and to reduce manufacturing costs.

Furthermore, it is desirable to fabricate silver-containing electronics onto polymeric or similar temperature-sensitive substrates by solution-based printing processes. Metallic electrically-conductive wires or grids of low resistance must be achieved at sufficiently low temperatures to be compatible with organic electronics on polymeric substrates. Among various known methods for fabricating electrically-conductive silver grids or patterns, the direct printing of silver-containing inks provides attractive prospects for making such electrically-conductive patterns.

Inkjet printing and flexographic printing have also been proposed for providing patterns of silver or silver-containing compounds, requiring the careful fabrication of a silver-containing paste or "ink" with desirable surface tension, viscosity, stability, and other physical properties required for such application processes. High silver content has generally been required for high electrical conductivity, and calcination or sintering may be additionally required for increasing electrical conductivity of printed silver inks.

Some approaches to providing silver metal is to employ a chemical ink formulation where the silver source is a molecular precursor or cation (such as a silver salt) that is then chemically reacted (or reduced) to produce silver metal. Electrically-conductive inks that are in the form of a chemical solution rather than as a suspension or dispersion of metal particles, have gained interest in recent years. One conductive ink of this type is known as a Metalorganic Decomposition (MOD) variety ink, for example, as described by Jahn et al. [*Chem. Mater.* 22, 3067-3071 (2010)] who investigated silver printing using an aqueous transition metal complex [$AgO_2C(CH_2OCH_2)_3H$]-containing MOD ink. They reported the formation of metallic silver features having electrical conductivities as high as $2.7 \times 10^7$ $S\ m^{-1}$, which corresponds to an electrical conductivity that is 43% of that of bulk silver, although a sintering temperature of 250° C. was required.

U.S. Patent Application Publication 2015/0004325 (Walker et al.) describes a chemically-reactive silver ink composition comprised of a complex of a silver carboxylate salt and an alkylamine, in which the complex is used to form an electrically-conductive silver structure at a temperature of 120° C. or less. Unfortunately, even these temperatures render the ink incompatible with many polymeric and paper substrates used in flexible electronic and biomedical devices. Furthermore, since alkylamines are known to reduce silver at room temperature, long term stability of such compositions is tentative. Furthermore, the publication teaches long heating times were needed to obtain low resistivity in the resulting articles.

Other industrial approaches to preparing electrically-conductive films or elements have been directed to formulating and applying photocurable compositions containing dispersions of metal particles such as silver metal particles to substrates, followed by curing the photocurable components in the photocurable compositions. The applied silver particles in the cured compositions can act as catalytic (seed) particles for electrolessly plated electrically-conductive metals. Useful electrically-conductive grids prepared in this manner are described for example, in U.S. Pat. Nos. 9,188, 861 (Shukla et al.) and 9,207,533 (Shukla et al.) and in US Patent Application Publications 2014/0071356 (Petcavich) and 2015/0125596 (Ramakrishnan et al.). Using these methods, photocurable compositions containing catalytic silver particles can be printed and cured on a suitable transparent substrate, for example, a continuous roll of a transparent polyester film, and then electroless metal plating can be carried out on the catalytic silver particles. However, these methods require that high quantities of purchased silver particles be uniformly dispersed within the photocurable compositions so that coatings or printed patterns have a sufficiently high concentration of catalytic sites. Without effective dispersing, silver particles readily agglomerate, leading to less ineffective electroless plating and electrical conductivity.

Moreover, forming stable patterns of silver particles in this manner requires the presence of photosensitive components such as polymerizable monomers or cross-linkable polymers that must be exposed to suitable radiation. Scaling such curing procedures to high volume use can be difficult and hard to reproduce on a consistent scale, especially to produce fine line electrically-conductive meshes or grids where the uniformity and size of fine lines are subjected to highly rigorous standards.

Efforts are being directed in the industry to avoid the need for photocuring. For example, U.S. Patent Application Publication 2012/0225126 (Geckeler et al.) describes a solid-state method for preparing silver nanoparticles using a mixture of a silver salt and a water-soluble polymer such as a starch or cellulose derivative that acts as a silver ion reducing agent. The mixture is milled by a high-speed vibration milling process to form silver nanoparticles within the water-soluble starch or cellulosic polymer so that a solvent is not needed for synthesis or transportation of the silver nanoparticles.

Various methods have been employed in the production of silver nanoparticles, such as co-precipitation methods in an aqueous solution, electrochemical methods, aerosol methods, reverse microemulsion methods, chemical liquid deposition methods, photochemical reduction methods, chemical reduction methods in a solution and UV irradiation methods. However, the conventional technologies have difficulties in the control of particle sizes and large-scale production of particles.

There are a variety of methods for producing nanometer-sized metallic nanoparticles. For example, U.S. Pat. No. 6,572,673 (Lee et al.) discloses a process for preparing metal nanoparticles, comprising reacting suitable metal salts and anionic surfactant containing an anionic group such as a carboxylic group, sulfate group, or sulfonate group as reducing agent in water under reflux at a temperature of 50-140° C. Such processes are carried out in aqueous solutions.

U.S. Pat. No. 9,005,663 (Raghuraman et al.) discloses a method for making silver nanoparticles, comprising reacting a silver salt with a phosphene amino acid. However, the phosphene amino acid reactant is an expensive material.

U.S. Pat. No. 7,892,317 (Nia) discloses a process for the synthesis of silver nano particle, consisting of reacting silver salt and an anionic surfactant, or a nonionic surfactant, and a reducing agent in an aqueous solution at room temperature.

U.S. Pat. No. 9,496,068 (Kurihara et al.) discloses a process for the synthesis of amine coated silver nano particles via thermal decomposition of oxalate ion-alkylamine-alkyl diamine-silver complex.

U.S. Patent Application Publication 2010/0040863 (Li) discloses a process for producing carboxylic acid-stabilized silver nanoparticles by heating a mixture of a silver salt long alkyl chain carboxylic acid and a tertiary amine in methanol.

U.S. Patent Application Publication 2014/0312284 (Liu et al.) discloses a process for producing an organoamine stabilized silver nanoparticle by reduction of silver salts with hydrazine in methanol. However, hydrazine is a toxic material and it would not be desirable to include it in a manufacturing process.

Cellulose is a polydisperse linear homopolymer consisting of regioselective and enantioselective β-1,4-glycosidic linked D-glucose units. The homopolymer contains three reactive hydroxyl groups at the C-2, C-3 and C-6 atoms that are in general, accessible to the typical chemical conversions of primary and secondary —OH groups.

The use of cellulose together with its derivatives has wide spread applications, for example in fibers, films, plastics, coatings, suspension agents, composites. With the advent of synthetic polymers, their uses have somewhat diminished, but cellulose derivatives are still the raw materials of choice for some uses. In addition, various studies are on-going to look for and expand their use in existing and new technologies. Cellulosic polymers can be considered renewable resources in some instances. An inherent problem that faces users of cellulosic polymers is their general insolubility in most common solvents. Modifying the structure of cellulosic polymers can improve their solubility, leading to the synthesis of various cellulose derivatives (cellulosics) that come in all forms and structures depending on the functional group(s) used in place of the hydroxyl groups on the cellulose chain.

For example, cellulose derivatization can involve partial or full esterification or etherification of the hydroxyl groups on the cellulose chain by reaction with various reagents to afford cellulose derivatives like cellulose esters and cellulose ethers. Among all cellulose derivatives, cellulose acetate is recognized as the most important organic ester of cellulose owing to its extensive industrial and commercial importance. Properties of cellulose derivatives (esters and ethers) are determined primarily by the functional group. However, they can be modified significantly by adjusting the degree of functionalization and the degree of polymerization of the polymer backbone to modify solubility in various solvents.

The solution properties of cellulose acetates have been well studied and have been shown to be influenced by the average degree of substitution and the distribution of substituents along the chain. Previous work on the gelation mechanism of cellulose acetate has shown interesting behavior with respect to the sol-gel transition. Cellulose acetate gels exhibit thermally reversible properties that depend on factors such as concentration, acetyl content, and the type of solvent. It is usually difficult to predict if cellulose will gel in a given organic solvent, and in most cellulose acetate/ solvent systems, gelation occurs after the solution is heated to a specific temperature and subsequently cooled. For example, Kwon et al., *Bull. Korean Chem. Soc.* 26(5), 837-840 describe a study of silver nanoparticles in cellulose acetate solutions.

U.S. Ser. No. 15/456,686 (noted above) describes a method for preparing articles using silver nanoparticles that are obtained by thermal reduction of reducible silver ions in the presence of certain cellulosic polymers. Despite all the various approaches and efforts to provide electrically-conductive silver in various consumer and industrial articles described above, there remains a need for simpler and less expensive compositions and methods for generation of silver nanoparticles in a fashion suitable particularly for pattern formation in high speed manufacturing processes.

Although, as described above, a number of methods to make silver nanoparticles and compositions containing them are known, a number of challenges remain which need to be addressed before such compositions can be used in printed electronic applications. For example, there remains a need for an expeditious method of making silver nanoparticles that doesn't require toxic reagents and solvents; for dispersing agents that are inexpensive and environmentally benign; for a method for large scale manufacturing and storage of silver nanoparticles; and for an efficient way of re-dispersibility of manufactured silver nanoparticles in environmentally friendly solvents.

SUMMARY OF THE INVENTION

The present invention provides a non-aqueous silver precursor composition consisting essentially of:

(a) one or more polymers selected from one or more of cellulose acetate, cellulose acetate phthalate, cellulose acetate butyrate, cellulose acetate propionate, cellulose acetate trimellitate, hydroxypropylmethyl cellulose phthalate, methyl cellulose, ethyl cellulose, hydroxyethyl cellulose, hydroxypropylmethyl cellulose, and carboxymethyl cellulose;

(b) reducible silver ions that are present at a weight ratio to the one or more (a) polymers of at least 5:1 and up to and including 50:1;

(c) one or more organic solvents, each of which has a boiling point at atmospheric pressure of at least 100° C. and up to but less than 500° C., wherein the Hansen parameter ($\delta_T^{Polymer}$) of each of the one or more polymers is less than or equal to the Hansen parameter ($\delta_T^{Solvent}$) of each of the one or more organic solvents; and (d) a nitrogenous base having a pKa in acetonitrile of at least 15 and up to and including 25 at 25° C., the (d) nitrogenous base being present in an equimolar amount or molar excess in relation to the amount of (b) reducible silver ions.

The present invention provides a non-aqueous silver precursor composition for use in a simple, safe, and inexpensive way to generate a non-aqueous dispersion of silver nanoparticles. Such non-aqueous silver precursor composition comprises reducible silver ions, a cellulosic polymer, and a nitrogenous base. The method for generating the silver nanoparticles can be readily and safely carried out to provide high weight fraction, fully dispersed silver nanoparticles that have long term stability because the silver nanoparticles do not readily agglomerate in the relatively benign organic solvents. These silver nanoparticle-containing compositions can be easily deposited or formed into patterns for various uses.

The present invention provides these advantages by means of using a nitrogenous base to facilitate faster silver ion reduction in the presence of the cellulosic polymer. The cellulosic polymers and organic solvents used in the non-aqueous silver precursor compositions also facilitate silver ion reduction and provide physical stability of the resulting silver nanoparticles using inexpensive and environmentally safe dispersing agents. The inventive compositions and methods can thus be used to provide compositions or dispersions of silver nanoparticles that can be used in various ways, for example, as applied to a substrate in a pattern for further processing.

Other advantages of the present invention would be readily apparent to one skilled in the art in view of the teaching provided herein.

DETAILED DESCRIPTION OF THE INVENTION

Figure 1:
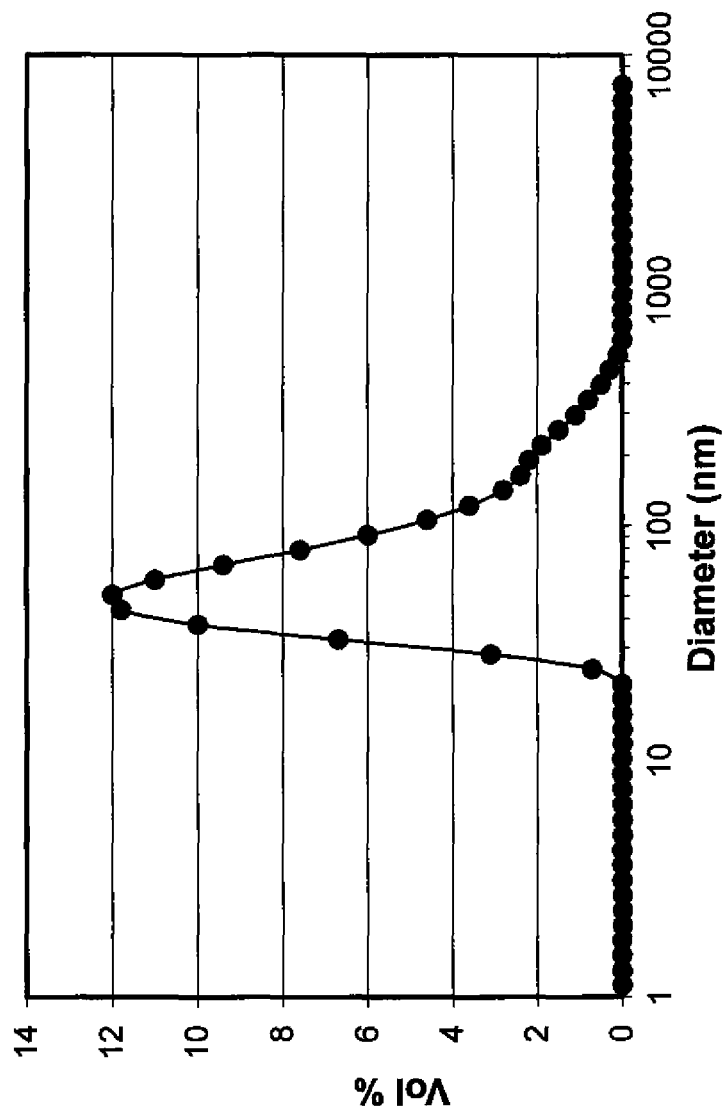
FIG. 1 is a graphical representation of particle size distribution as described below in Invention Example 1.

The following discussion is directed to various embodiments of the present invention and while some embodiments can be desirable for specific uses, the disclosed embodiments should not be interpreted or otherwise considered be limit the scope of the present invention, as claimed below. In addition, one skilled in the art will understand that the following disclosure has broader application than is explicitly described and the discussion of any embodiment.

Definitions

As used herein to define various components of the non-aqueous silver precursor composition, unless otherwise indicated, the singular forms "a," "an," and "the" are intended to include one or more of the components (that is, including plurality referents).

Each term that is not explicitly defined in the present application is to be understood to have a meaning that is commonly accepted by those skilled in the art. If the construction of a term would render it meaningless or essentially meaningless in its context, the term definition should be taken from a standard dictionary.

The use of numerical values in the various ranges specified herein, unless otherwise expressly indicated otherwise, are approximations as though the minimum and maximum values within the stated ranges were both preceded by the word "about." In this manner, slight variations above and below the stated ranges can be used to achieve substantially the same results as the values within the ranges. In addition, the disclosure of these ranges is intended as a continuous range including every value between the minimum and maximum values.

Unless otherwise indicated, the term "weight %" refers to the amount of a component or material based on the total amount of a non-aqueous silver precursor composition or non-aqueous dispersion. In other embodiments, "weight %" can refer to the % solids (or dry weight) of a dry layer, coating, thin film, or silver-containing pattern.

Unless otherwise indicated, the term "non-aqueous" as applied to the compositions and dispersions according to the present invention means that solvent media used to form such compositions are predominantly organic in nature and water is not purposely added but may be present in an amount of less than 10 weight % by virtue of being part of a chemical component, or particularly less than 5 weight %, or even less than 1 weight %, of the total weight of all solvents in the composition.

Unless otherwise indicated, the term "non-aqueous silver precursor composition" means that the silver present therein is predominantly (greater than 50 weight % of total silver) in the form of reducible silver ions.

The average dry thickness of silver nanoparticle-containing lines, grid lines, or other pattern features described herein can be the average of at least 2 separate measurements taken, for example, using electron microscopy, optical microscopy, or profilometry all of which should provide substantially the same results for the same test sample.

The use of "dry" in reference to thickness and width of lines, patterns, or layers, refers to embodiments in which at least 80 weight % of originally present organic solvent(s) has been removed.

As used herein for defining silver nanoparticles, "mean particle size" is measured using dynamic light scattering (DLS), that is sometimes referred to as Quasi-Elastic Light Scattering (QELS), and is a well-established technique for measuring the size and size distribution of molecules and particles typically in the submicron region, and even lower than 1 nm. Commercial DLS instruments are available from, for example, Malvern and Horiba who also supply instructions for use of such equipment, and such equipment and accompany instructions can be used to characterize and carry out the present invention.

The boiling point of organic solvents described herein can be determined from known publications or measured using standard methods.

Unless otherwise indicated herein, viscosity can be determined at 25° C. using any standard commercially available viscometer.

Unless otherwise indicated, the term "group" particularly when used to define a substituent or a moiety, can itself be substituted or unsubstituted (for example an "alkyl group" refers to a substituted or unsubstituted alkyl group) by replacement of one or more hydrogen atoms with suitable substituents (noted below) such as a fluorine atom. Generally, unless otherwise specifically stated, substituents on any "groups" referenced herein or where something is stated to be possibly substituted, include the possibility of any groups, whether substituted or unsubstituted, which do not destroy properties necessary for the utility of the component or non-aqueous silver precursor composition. It will also be understood for this disclosure and claims that reference to a compound or complex of a general structure includes those compounds of other more specific formula that fall within the general structural definition. Examples of substituents on any of the mentioned groups can include known substituents such as halogen (for example, chloro and fluoro); alkoxy, particularly those with 1 to 5 carbon atoms (for example, methoxy and ethoxy); substituted or unsubstituted alkyl groups, particularly lower alkyl groups (for example, methyl and trifluoromethyl), particularly either of those having 1 to 6 carbon atoms (for example, methyl, ethyl, and t-butyl); and other substituents that would be readily apparent in the art.

Unless otherwise indicated, the terms "total Hansen solubility parameter" and "total Hansen parameter" refer to the same thing. Hansen Solubility Parameters (also named reverse solvency principle) were developed by Charles Hansen as a way of predicting if one material will dissolve in another and form a solution. They are based on the concept that "like dissolves like" where one molecule is defined as being "like" another if it bonds to itself in a similar way. Each chemical molecule is given three Hansen parameters, each generally measured in $Mpa^{0.5}$: $\delta_d$, the energy from dispersion bonds between molecules; $\delta_p$, the energy from polar bonds between molecules; and $\delta_h$, the energy from hydrogen bonds between molecules. The "total Hansen solubility parameter" is defined as:

$$\delta^2 = \delta_d^2 + \delta_p^2 + \delta_h^2$$

These three Hansen parameters can be treated as co-ordinates for a point in three dimensions also known as the Hansen space. The nearer that two molecules are in this three dimensional space, the more likely they are to dissolve into each other. To determine if the total Hansen parameters of two molecules (usually a solvent and a polymer) are within range, a value called the interaction radius ($R_0$) is given to the substance being dissolved. This interaction radius determines the radius of the sphere in the Hansen space and its center is the three Hansen parameters. In order to calculate the distance (Ra) between the Hansen parameters in the Hansen space the following formula is used:

$$R_a^2 = 4(\delta_{d1} - \delta_{d2})^2 + (\delta_{p1} - \delta_{p2})^2 + (\delta_{h1} - \delta_{h2})^2$$

The concept of a total Hansen parameter is well understood by anyone skilled in the art. A detailed description of the derivation and theory is found in various references such as (1) A. F. M. Barton, "Handbook of Polymer-Liquid Interaction Parameters and Solubility Parameters," CRC Press Inc. (1990) and (2) Solubility Parameter Values, Eric A. Grulke, Polymer Handbook, John Wiley and Sons, Inc. (1989). In many instances, the total Hansen parameter of each useful polymer can be obtained from product literature where available, estimated from studies of similar materials as published in the Handbook of Polymer-Liquid Interaction Parameters and Solubility Parameters, by Allan F. M. Barton, CRC Press (1990), or determined by solubility studies. The total Hansen parameters of organic solvent mixtures can be calculated using the sum of volume fractions of the individual organic solvent components in the premix solution. Total Hansen parameters as well as the three-component Hansen parameters for dispersive, polar, and hydrogen-bonding components of the solubility parameter, are readily available in the literature.

Uses

The deposition or patterning of functional electrodes, pixel pads, and conductive traces, lines, and tracks, that meets electrical conductivity, processing, and cost requirements for practical applications has been a great challenge. Silver metal is of interest in the preparation of electrically-conductive elements for use in electronic devices with or without further electroless plating.

The non-aqueous silver-containing dispersions described herein can be used for forming metallic silver patterns and electrodes for example in membrane touch switches (MTS), battery testers, biomedical, electroluminescent lamps, radio frequency identification (RFID) antenna, flat panel displays such as plasma display panel (PDP) and organic light emitting diode (OLED) displays, printed transistors and thin film photovoltaics, and thereby reduce the number of steps for pattern formation in such devices.

The non-aqueous silver precursor compositions described herein have actual and potential uses in various technologies and industries. Most specifically, they can be used to provide silver metal for various purposes, including but not limited to, the formation of electrically-conductive grids or patterns of fine wires or other geometric forms, the formation of silver seed particles for electroless plating with other electrically-conductive metals, and the formation of silver in various materials for antimicrobial activity.

More specifically, the non-aqueous silver precursor compositions according to the present invention are useful to provide silver metal in non-aqueous dispersions that in turn can be used to provide electrically-conductive metal patterns. These electrically-conductive metal patterns can be incorporated into various devices including but not limited to, touch screens or other transparent display devices, and in modern electronics such as solar cell electrodes, electrodes in organic thin film transistors (OTFTs), flexible displays, radio frequency identification tags, light antennas, and other devices that would be readily apparent to one skilled in the art.

Non-Aqueous Silver Precursor Compositions

For all embodiments, the non-aqueous silver precursor compositions according to the present invention contain four essential components for purposes of providing silver metal in the form of silver nanoparticles according to the present invention: one or more (a) polymers (such as one or more cellulosic polymers) as described below; (b) reducible silver ions in the form of one or more silver salts or silver complexes as described below; an organic solvent medium consisting of (c) or more organic solvents, as described below; and (d) one or more nitrogenous bases, as described below. No other components are purposely added to the non-aqueous silver precursor compositions according to the present invention to achieve the inventive purposes or advantages, and as noted above, water is not purposely included. As described below, for some embodiments, (e) carbon black can be present as a fifth essential component.

Upon thermal treatment, as described below, the non-aqueous silver precursor composition according to this invention can be converted into a corresponding non-aqueous dispersion or non-aqueous silver-containing dispersion comprising a silver nanoparticle composite comprising both silver and one or more polymers as described below. It is desirable that at least 90 mol %, at least 95 mol %, or even at least 98 mol % (which means "substantially all") of the (b) reducible silver ions are converted to silver during this process.

The one or more (a) polymers, (b) reducible silver ions, (c) organic solvents, and nitrogenous bases can be combined in general by mixing them under suitable ambient conditions so that thermal reduction does not occur prematurely to any appreciable extent. In some embodiments, the (a), (c), and (d) components can be formulated or mixed to form a premix solution and under appropriate heating, the (b) reducible silver ions can be added the premix solution in a controlled fashion. Alternatively, the (a), (b), and (c) components can be formulated or mixed to form a premix solution, and the (d) nitrogenous base can be added to the premix solution in a controlled fashion. Details of these methods are described below.

Ultimately, the non-aqueous silver precursor composition is formed, and it generally has a % solids of at least 1% and up to and including 50%, or more typically of at least 5% and up to and including 20%. The amount of solids, and (c) organic solvents, and viscosity, can thus be adjusted for a particular use or silver ion reduction operation.

The non-aqueous silver precursor composition is generally in liquid form having a viscosity of at least 1 centipoise (0.001 Pascal sec) and up to and including 5,000 centipoise (5 Pascal sec), or more likely a viscosity of at least 3 centipoise (0.003 Pascal sec) and up to and including 50 centipoise (0.05 Pascal sec), all measured at 25° C.

The non-aqueous (silver-containing) dispersion described below can have the same or different viscosity as the corresponding non-aqueous silver precursor composition. In most embodiments, the two compositions have essentially the same viscosity, that is, no more than 10% difference.

(a) Polymers:

The polymers useful in the practice of the present invention are organic in nature and can be used singly or in mixtures of two or more different materials. When used in mixtures, the two or more different materials can be present in the same or different amounts within the total polymer amount. Both cellulose esters and cellulose ethers can be used in the present invention.

Representative useful polymers for the practice of the present invention are selected from cellulose acetate, cellulose acetate phthalate, cellulose acetate butyrate, cellulose acetate propionate, cellulose acetate trimellitate, hydroxypropylmethyl cellulose phthalate, methyl cellulose, ethyl cellulose, hydroxyethyl cellulose, hydroxypropylmethyl cellulose, carboxymethyl cellulose, and mixtures of two or more of such materials.

Particularly useful polymers according to the present invention include carboxymethyl cellulose, cellulose acetate butyrate, cellulose acetate propionate, ethyl cellulose, and cellulose acetate, individually or in mixtures.

It can also be useful to use cellulosic polymers such as cellulose esters that comprise free hydroxy groups directly attached to the polymer backbone to provide a free hydroxyl content in an amount of at least 1%, or at least 2%, and up to and including 5%, based on the total hydroxy groups that could potentially be present in the polymer. The remaining hydroxy groups in the molecule would be esterified so that there is relatively low free hydroxyl content.

The one or more (a) polymers can be present in a total amount of at least 1 weight % and up to and including 25 weight %, or more likely of at least 3 weight % and up to and including 10 weight %, based on the total weight of silver in the non-aqueous silver precursor composition.

Each of the useful polymers can be readily obtained from various commercial sources, or in some cases, they can be prepared using known starting materials, reaction conditions, and known synthetic procedures.

(b) Reducible Silver Ions:

Reducible silver ions can be provided in the non-aqueous silver precursor composition from many sources as long as each silver salt or silver complex in which they are provided is soluble within the one or more (c) hydroxylic organic solvents at an amount of at least 1 g/liter at 20° C.

In general, silver salts or silver complexes comprised of reducible silver ions and any suitable organic or inorganic anion or complexed moiety (or a combination of anions and complexed moieties) can be used in the practice of the present invention to provide the (b) reducible silver ions for the present invention. Such silver complexes can be mononuclear, dinuclear, trinuclear, or higher and each compound generally has a net neutral charge. The following classes of useful reducible silver ion-containing salts and reducible silver ion-containing complexes are described as representative materials, but the present invention is not to be interpreted to be limited to them. Such reducible silver ion-containing materials can be readily purchased from various commercial sources or prepared using known procedures, starting materials, and reaction conditions unless otherwise indicated.

(i) A first class of reducible silver ion-containing compounds are silver salts having organic or inorganic anions. Some representative silver salts include but not limited to, silver nitrate, silver acetate, silver benzoate, silver nitrite, silver thiocyanate, silver myristate, silver citrate, silver phenylacetate, silver malonate, silver succinate, silver adipate, silver phosphate, silver perchlorate, silver acetylacetonate, silver lactate, silver salicylate, silver oxalate, silver 2-phenylpyridine, silver trifluoroacetate; silver fluoride and silver fluoride complexes such as silver (I) fluorosulfate, silver (I) trifluoromethane sulfate, silver (I) pentafluoropropionate, and silver (I) heptafluorobutyrate; β-carbonyl ketone silver (I) complexes; silver proteins; and derivatives of any of these materials.

(ii) Complexes of hindered aromatic N-heterocycle with (b) reducible silver ions can be used in the practice of this invention. The term "hindered" as used to define hindered aromatic N-heterocycle means that the moiety has a "bulky"

group located in the α position to the nitrogen atom in the aromatic ring. Such bulky groups can be defined using the known "A-value" parameter that is a numerical value used for the determination of the most stable orientation of atoms in a molecule (using conformational analysis) as well as a general representation of steric bulk. A-values are derived from energy measurements of a mono-substituted cyclohexane ring. Substituents on a cyclohexane ring prefer to reside in the equatorial position to the axial. In the present invention, the useful "bulky" groups in the hindered aromatic N-heterocycle have an A-value of at least 0.05. Useful reducible silver ion-containing complexes of this type are described in U.S. Pat. No. 9,377,688 (Shukla), the disclosure of which is incorporated herein by reference for a further description of properties, representative compounds, and methods for preparing them.

(iii) Other useful complexes comprise (b) reducible silver ions are silver carboxylate-trialkyl, carboxylate-triaryl, and carboxylate-alkylaryl phosphite complexes and mixtures of these compounds. The terms "carboxylate-trialkyl phosphite" and "carboxylate-triaryl phosphite" are to be interpreted herein as indicating that the complex of which it is a part can have three of the same or different alkyl groups, or three of the same or different aryl groups, respectively. The term "carboxylate-alkylaryl phosphite" refers to a compound having a mixture of a total of three alkyl and aryl groups, in any combination. Useful reducible silver ion-containing complexes of this type are described in U.S. Pat. No. 9,375,704 (Shukla), the disclosure of which is incorporated herein by reference for a further description of properties, representative compounds, and methods for preparing them.

(iv) Silver-oxime complexes can be used to provide (b) reducible silver ions, and these materials are generally non-polymeric in nature (meaning that the silver complex molecular weight is less than 3,000). Useful non-polymeric silver-oxime complexes of this type are described in U.S. Pat. No. 9,387,460 (Shukla), the disclosure of which is incorporated herein by reference for a further description of properties, representative compounds, and methods for preparing them.

(v) Other useful silver complexes comprising (b) reducible silver ions can be represented by the following Structure (V):

$$(Ag^+)_a(L)_b(P)_c \qquad (V)$$

wherein L represents an α-oxy carboxylate; P represents a 5- or 6-membered N-heteroaromatic compound; a is 1 or 2; b is 1 or 2; and c is 1, 2, 3, or 4, provided that when a is 1, b is 1, and when a is 2, b is 2.

Each of the complexes of Structure (V) comprises one or two reducible silver ions. Each reducible silver ion is complexed with one or two α-oxy carboxylate compounds that can be via two oxygen atoms provided from the same molecule of an α-oxy carboxylate compound, or oxygen atoms provided from two molecules of the same or different α-oxy carboxylate compounds.

The α-oxy carboxylate groups (moieties or components) can be defined in which the α-carbon atom attached directly to the carboxyl group [—C(=O)O—] has a hydroxy group, oxy, or an oxyalkyl substituent group. Thus, the α-oxy carboxylates can be either α-hydroxy carboxylates, α-alkoxy carboxylates, or α-oxy carboxylates. With the α-hydroxy carboxylates and α-alkoxy carboxylates, the remainder of the valences of that α-carbon atom can be filled with hydrogen or a branched or linear alkyl group (substituted or unsubstituted) as described below in more detail. In addition, the α-oxy carboxylate (L) generally has a molecular weight of 250 or less, or 150 or less.

In Structure (V) shown above, b is 1 or 2, and in the embodiments where b is 2, the two α-oxy carboxylate compounds within a single complex molecule can be the same or different compounds. In some embodiments of the present invention, L of Structure (V) described above can be represented by the following Structure (VI):

wherein $R_1$, $R_2$, and $R_3$ are independently hydrogen or branched or linear alkyl groups. In most embodiments, at least one of $R_1$ through $R_3$ is a branched or linear alkyl group having from 1 to 8 carbon atoms, and any of the hydrogen atoms in such branched or linear alkyl groups can be replaced with a heteroatom such as a fluorine atom substituent.

Some particularly useful conjugate acids from which α-oxy carboxylates (L) of Structure (VI) can be selected from the group consisting of lactic acid, 2-hydroxybutyric acid, 2-hydroxy-3-methylbutyric acid, 2-hydroxy-3,3-dimethylbutyric acid, 2-hydroxy-isobutyric acid, 2-hydroxy-2-methylbutyric acid, 2-ethyl-2-hydroxybutyric acid, 2-hydroxy-2,3-dimethylbutyric acid, 2-ethyl-2-methoxybutyric acid, 2-methoxy-2-methylpropanoic acid, 1-hydroxycyclopentane-1-carboxylic acid, 2,3-dihydroxy-2,3-dimethylsuccinic acid, and 2,4-dihydroxy-2,4-dimethylpentanedioic acid. As noted above, mixtures of these materials can be used in a specific complex if desired.

In other embodiments, L is represented in Structure (V) by the following Structure (VII):

wherein $R_4$ is a branched or linear alkyl group having 1 to 8 carbon atoms, including branched iso- and tertiary alkyl groups having 3 to 8 carbon atoms. In addition, any of the hydrogen atoms in any of the branched or linear alkyl groups optionally can be replaced with a fluorine atom; for example, the terminal carbon atom of a $R_4$ branched or linear alkyl group can have 1 to 3 fluorine atoms.

Some useful conjugate acids from which the α-oxy carboxylate (L) represented by Structure (VII) can be selected from the group consisting of pyruvic acid, 3-methylpyruvic acid, 3,3-dimethylpyruvic acid, 3,3-dimethyl-2-oxobutanoic acid, 3,3-dimethyl-2-oxopentanoic acid, and 2,3-dioxosuccinic acid.

The "P" compound of Structure (V) is a 5- or 6-membered N-heteroaromatic compound such as a 6-membered N-heteroaromatic compound. Such 5- or 6-membered N-heteroaromatic compounds can have a $pK_a$ of at least 10 and up to and including 22. An experimental method for measuring $pK_a$ and the $pK_a$ values of some N-heteroaromatic bases are known (for example, see Kaljurand et al. *J. Org. Chem.* 2005, 70, 1019).

In general, each 5- or 6-membered N-heteroaromatic compound is non-polymeric in nature and has a molecular weight of 200 or less. By "5- or 6-membered," it is meant that the N-heteroaromatic compound has either 5 or 6 atoms in the heterocyclic aromatic ring, at least one of which atoms is a nitrogen atom. In general, such heterocyclic aromatic rings generally have at least one carbon atom and at least one nitrogen atom in the ring.

In Structure (V) shown above, c is 1, 2, 3, or 4, and in the embodiments where c is 2, 3, or 4, the multiple 5- or 6-membered N-heteroaromatic compound molecules within the single complex molecule can be the same or different. For example, the 5- or 6-membered N-heteroaromatic compound can be selected from the group consisting of pyridine, 2-methylpyridine,4-methylpyridine, 2,6-dimethylpyridine, 2,3-dimethylpyridine, 3,4-dimethylpyridine, 4-pyridylacetone, 3-chloropyridine, 3-fluoropyridine, oxazole, 4-methyloxazole, isoxazole, 3-methylisoxazole, pyrimidine, pyrazine, pyridazine, and thiazole.

Representative 5- or 6-membered N-heteroaromatic compounds can be readily obtained from various commercial chemical suppliers located in various countries.

Further details of properties, representative compounds, and methods of making them are provided in copending and commonly assigned U.S. Ser. No. 15/231,804 (filed Aug. 9, 2016 by Shukla), the disclosure of which is incorporated herein by reference. Of these types of reducible silver ion-containing complexes, a silver α-oxycarboxylate pyridine complex such as silver lactate pyridine complex, is particularly useful.

(vi) Still other useful silver complexes are designed with one or two (b) reducible silver ions as described above for the (iv) silver complexes, complexed with both one or two α-oxy carboxylate molecules as described above for the (iv) silver complexes, and one, two, three, or four primary alkylamine molecules. In general, such useful silver complexes can be represented by the following Structure (VIII):

(VIII)

wherein L represents the α-oxy carboxylate; P represents the primary alkylamine; a is 1 or 2; b is 1 or 2; and c is 1, 2, 3, or 4, provided that when a is 1, b is 1, and when a is 2, b is 2.

In such complexes, P is a primary alkylamine having a boiling point of less than or equal to 175° C., or having a boiling point of less than or equal to 125° C., or even at least 75° C. and up to and including 125° C., at atmospheric pressure. The useful primary alkyl amines that generally have a molecular weight of less than 500 and are thus considered "non-polymeric" as defined by molecular weight and boiling point.

The term "primary alkylamine" refers herein to compounds that are non-aromatic and are not cyclic in structure. They generally have one or more nitrogen atoms as long as all other features (molecular weight, pKa, boiling point, and oxidation potential) described herein are met. In such compounds, each of the nitrogen atoms has two valences filled by hydrogen atoms and the remaining valence of each nitrogen atom is filled with a substituted or unsubstituted alkyl group (not including alkylaryl groups such as benzyl groups), or with a substituted or unsubstituted alkylene group for compounds defined herein as "primary alkyl diamines" that can be illustrated by the following Structure (IX):

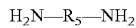 (IX)

wherein $R_5$ represents a substituted or unsubstituted, branched or linear, divalent alkylene group having 1 to 5 carbon atoms; and optional substituents include but are not limited to, fluoride atoms for any of the hydrogen atoms in the alkylene group.

In most useful embodiments, the primary alkyl amines comprise a single nitrogen atom and a single substituted or unsubstituted, branched or linear alkyl group having at least 3 carbon atoms, and generally from 3 to 6 carbon atoms, wherein any of the hydrogen atoms of the alkyl group can be replaced with a fluorine atom.

Representative useful primary alkylamines can be selected from the group consisting of a propylamine, n-butylamine, t-butylamine, isopropylamine, 2,2,2-trifluoroethylamine, 2,2,3,3,3-pentafluoropropylamine, 3,3,3-trifluoropropylamine, 1,2-dimethylpropylamine, t-amyl amine, and isopentylamine. Other useful primary alkylamines would be readily apparent to one skilled in the art. In some embodiments, the primary amine has an asymmetric carbon center on an alkyl chain. Some examples of such amines include but not limited to, a 2-amino-3-methylbutane, 3,3-dimethyl-2-butylamine, 2-aminohexane, sec-butylamine, and others that would be readily apparent to one skilled in the art from the foregoing description. Such primary alkylamines can be substituted with other groups that would be readily apparent to one skilled in the art.

Useful primary alkyl amines can be readily obtained from various worldwide commercial sources of chemicals.

Further details of properties, representative compounds, and methods of making them are provided in copending and commonly assigned U.S. Ser. No. 15/231,837 (filed Aug. 9, 2016 by Shukla), the disclosure of which is incorporated herein by reference.

(vii) Yet other useful reducible silver ion-containing complexes are designed with one or two (b) reducible silver ions as described above for the (iv) silver complexes, complexed with both one or two α-oxy carboxylate molecules as described above for the (iv) silver complexes, and one, two, three, or four oxime compound molecules. In general, each useful silver complex can be represented by the following Structure (X):

 (X)

wherein L represents the α-oxy carboxylate; P represents an oxime compound; a is 1 or 2; b is 1 or 2; and c is 1, 2, 3, or 4, provided that when a is 1, b is 1, and when a is 2, b is 2.

In the noted Structure (X), the "P" compound is an oxime compound (or a mixture of two or more different oxime compounds). Traditionally, an "oxime" has a general formula of >C=N—OH. In the present invention, the term "oxime compound" is meant to include such compounds as well as compounds in which the hydrogen is replaced with a suitable monovalent radical. In general, the oxime compounds useful herein are not polymeric in nature and each has a molecular weight of 200 or less, or of 150 or less.

In Structure (X) shown above, c is 1, 2, 3, or 4, and in the embodiments where c is 2, 3, or 4, the P molecules within the single complex molecule can be the same or different oxime compounds.

For many embodiments, P can be an oxime compound that can be represented by the following Structure (XI):

 (XI)

wherein $R_5$ and $R_6$ are independently hydrogen or a substituted or unsubstituted alkyl group having 1 to 6 carbon atoms (linear or branched), provided that at least one of $R_5$ and $R_6$ is one of such alkyl groups. Alternatively, $R_5$ and $R_6$ can together represent the carbon atoms sufficient to provide a substituted or unsubstituted 5- or 6-membered, saturated carbocyclic ring, such as a substituted or unsubstituted pentane ring or substituted or unsubstituted cyclohexane ring.

$R_7$ is hydrogen, a substituted or unsubstituted alkyl group having 1 to 6 carbon atoms (linear or branched), a substituted or unsubstituted acyl group having 1 to 6 carbon atoms (linear or branched), a —C(=O)$R_8$ group, or a carbonyloxyalkyl group [—C(=O)O$R_8$], wherein $R_8$ is hydrogen or a substituted or unsubstituted alkyl having 1 to 6 carbon atoms (linear or branched).

Representative oxime compounds useful in the practice of the present invention include but are not limited to, acetoxime (acetone oxime), acetaldoxime, Aldicarb, dimethylglyoxime, methylethyl ketone oxime, propionaldehyde oxime, cyclohexanone oxime, cyclopentanone oxime, heptanal oxime, acetone-O-methyl oxime, acetaldehyde-O-methyl oxime, propionaldehyde-O-methyl oxime, butanaldehyde-O-methyl oxime, 2-butanone-O-methyl oxime, cyclopentanone-O-methyl oxime, and 2-butanone-O-ethyl oxime.

Some representative oxime compounds can be readily obtained from various commercial chemical suppliers such as Sigma Aldrich. Further details of properties, representative examples, and methods of making them are provided in copending and commonly assigned U.S. Ser. No. 15/362,868 (filed Nov. 29, 2016 by Shukla et al.), the disclosure of which is incorporated herein by reference.

In the non-aqueous silver precursor composition, according to the present invention, the amounts of the (b) reducible silver ions can be varied depending upon the particular manner in which the composition is to be used. In general, the (b) reducible silver ions are present at a weight ratio to the one or more (a) polymers of at least 5:1 and up to and including 50:1, or even at least 5:1 and up to and including 20:1, as described above.

(c) Organic Solvents Used in Making of Silver Nanoparticles

The organic solvent(s) used in the practice of this invention are not particularly limited as long as the nitrogenous base and compounds containing (b) reducible silver ions can be readily dissolved or dispersed therein. It is useful that each (c) organic solvent used in the non-aqueous silver precursor composition or the non-aqueous silver-containing dispersion (described below) has a boiling point greater than or equal to 90° C., or at least 100° C., at least 150° C. and at least >200° C. but generally less than 500° C. If two or more different organic solvents are used, the difference of the boiling points of any two organic solvents can be greater than >10° C.

In the practice of the present invention, the (c) organic solvents useful in the practice of this invention can be selected to have a total Hansen parameter that is compatible with the total Hansen parameter of the one or more (a) polymers (such as one or more cellulosic polymers) that are to be incorporated into the silver nanoparticle composite. It is desirable that the total Hansen parameters of the one or more (a) polymers and the one or more (c) organic solvents lie within a certain range, and it is especially desirable to maintain the desired total Hansen parameter as the organic solvent profile changes during the deposition processes. Typically, the (c) organic solvents have a total Hansen parameter equal to or greater than the total Hansen parameter of the one or more (a) polymers (such as one or more cellulosic polymers). Thus, if a mixture of (c) organic solvents is used, it is desirable that the total Hansen parameter of the organic solvent mixture is equal to or greater than the total Hansen parameter of the one or more (a) polymers (such as one or more cellulosic polymers) to be incorporated within the silver nanoparticle composite. Some useful dispersions comprise organic solvent blends that maintain desirable total Hansen parameters even as the (c) organic solvents are removed during and after the deposition processes (described below).

Thus, in all embodiments of the non-aqueous silver precursor composition, the (a), (b), and (d) components are dispersed or dissolved in an (c) organic solvent medium that consists of one or more organic solvents described herein, and especially one or more hydroxylic organic solvents, each of which has an α-hydrogen atom and properties defined below. It is particularly useful that the (a) polymer(s) are soluble in the one or more (c) organic solvents.

Useful hydroxylic solvents can be alcohols having an α-hydrogen atom. Accordingly, primary and secondary alcohols are useful and they can be monohydric or polyhydric. While either saturated or unsaturated alcohols can be used, it is desirable that the alcohol used be free from olefinic unsaturation. Suitable alcohols can be of either straight-chain or branched-chain configuration, and can contain in their structure either or both of alicyclic or aromatic carbon-to-carbon moieties. Representative examples of suitable straight-chain primary alcohols include but are not limited to, ethanol, n-propanol, n-butanol, n-pentanol, n-hexanol, 1-octanol, 2-ethyl-1-hexanol, n-decanol, ethylene glycol, propylene glycol, and benzyl alcohol. Representative examples of branched-chain alcohols include isobutyl alcohol, isoamyl alcohol, and secondary butyl carbinol. Secondary alcohols have greater reactivity. Representative examples of secondary alcohols include but are not limited to, isopropyl alcohol, secondary butyl alcohol, secondary amyl alcohol, diethyl carbinol, methyl isobutyl carbinol, methyl-3-heptanol, diisobutyl carbinol, dodecanol-Z, methyl allyl carbinol, cyclohexanol, methyl cyclohexyl carbinol, phenyl methyl carbinol, and similar materials. Combinations of any of these alcohols can be used if desired. Such materials can be readily purchased from various commercial sources or readily prepared using known starting materials, conditions, and reaction schemes.

Glycol ethers with both an ether and alcohol functional group in the same molecule are particularly useful in the practice of the present invention. Representative examples of such glycol ethers include but are not limited to, 2-methoxyethanol, 2-ethoxyethanol, diethylene glycol monoethyl ether (carbitol), and methoxy isopropanol. Mixtures of these compounds can be used if desired. Such glycol ethers are commercially available.

Minor amounts of water can be present, but the total weight % of water in the non-aqueous silver precursor composition is generally less than 10%.

(d) Nitrogenous Bases:

Another essential component of the non-aqueous silver precursor compositions according to the present invention is a nitrogenous base having a pKa in acetonitrile of at least 15 and up to and including 25 at 25° C. Such one or more nitrogenous bases are generally present in an equimolar amount or molar excess relative to the amount of (b) reducible silver ions, described above.

In general, the nitrogenous bases can be cyclic or acyclic alkyl amines. All primary amines, secondary amines, or tertiary amines are useful in the present invention. Some especially useful amines are 1,4-diazabicyclo[2.2.2]octane (DABCO), cyclohexylamine, piperidine, N-methyl piperidine, N-methyl-3-piperidinol, and others that would be readily apparent to one skilled in the art. Combinations of two or more of these compounds can be used if desired.

The nitrogenous base can be an alkanolamines including but are not limited to, ethanol amine, 2-(ethylamino)ethanol, 2-(methylamino)ethanol, 2-(butylamino)ethanol, methyldiethanolamine (MDEA), diethanolamine (DEA), diglycolamine (DGA), diethylaminoethanol (DEAE), and others that would be readily apparent to one skilled in the art. Combinations of two or more of these compounds can be used if desired.

Nitrogen-containing heterocyclic compounds are also useful as nitrogenous bases in the present invention. Such compounds can be are aromatic and heterocyclic in nature and comprise at least one nitrogen atom in the aromatic heterocyclic ring. Such compounds can also be substituted or unsubstituted as desired. Representative aromatic heterocyclic, nitrogen-containing bases useful in this invention include but are not limited to, substituted or unsubstituted, non-polymeric pyridine, picolines, lutidines, quinoline, isoquinoline, imidazole, benzimidazole, benzthiazole, thiazole, oxazole, benzoxazole, 4,4'-bipyridine, pyrazine, triazine, pyrimidine, nicotinic acid, and isonicotinic acid compounds. Mixtures of two or more these or other unnamed compounds can be used if desired, in any useful proportion. The substituted or unsubstituted pyridines are particularly useful.

Other useful nitrogenous bases include amidines such as 1,8-diazabicyclo[5.4.0]undec-7-ene (DBU).

It is essential that the nitrogenous base has a pKa of at least 15 and up to and including 20, or more typically of at least 18 and up to and including 25, as measured in acetonitrile. An experimental method for measuring pKa, and the pKa values of some aromatic heterocyclic and amine nitrogenous bases are known (for example, see Kalijurand et al. *J. Org. Chem.* 2005, 70, 1019; and Cantu et al. *Journal of Chromatography A,* 2005, 1068, 99).

In general, each nitrogenous base used in the present invention is in liquid form and has a boiling point equal to or higher than each of the one or more (c) organic solvents, for example, each of the one or more hydroxylic solvents. Thus, the boiling point of the nitrogenous base at atmospheric pressure is at least 100° C. and up to but less than 500° C., or at least 120° C. and up to and including 350° C., or up to and including 250° C.

Useful nitrogenous bases can be readily obtained from commercial sources.

Non-Aqueous Silver-Containing Dispersions

The reducible silver ions in a non-aqueous silver precursor composition according to the present invention can be converted into silver nanoparticles in silver nanoparticle composites to provide a corresponding non-aqueous silver-containing dispersion using the operations described below for the methods according to this invention.

Such non-aqueous silver-containing dispersions comprise one or more silver nanoparticle composites, each comprising silver and one or more of the (a) polymers described above. The amount of such silver nanoparticle composites in the non-aqueous silver-containing dispersion would generally be the total weight of silver and (a) polymers in the non-aqueous silver-containing dispersion but it could be less, depending upon how much of the (b) reducible silver ions are reduced and how much free silver, (b) reducible silver ions, and free (a) polymers are present in the non-aqueous silver-containing dispersion after silver ion reduction, silver nanoparticle composite isolation, and re-dispersion (described below).

As noted above, it is desired that a high amount of the reducible silver ions be converted to silver metal and thus, the non-aqueous silver-containing dispersion would contain silver in an amount of up to and including 100 mol % of the original (b) reducible silver ions in the non-aqueous silver precursor composition.

The non-aqueous silver-containing dispersion contains one or more (c) organic solvents (such as hydroxylic organic solvents) as described above. Such organic solvents can be same or different as those used to make the non-aqueous silver precursor compositions. These (c) organic solvents can be those originally in the non-aqueous silver precursor composition (that is, before isolation and re-dispersion of the silver nanoparticle composite), or they can be added during re-dispersion of the silver nanoparticle composite.

(d) Nitrogenous base is also generally present in the non-aqueous silver-containing dispersion although much of the original amount that was present in the non-aqueous silver precursor composition may be washed out during isolation of the silver nanoparticle composite. However, it is evident that some (d) nitrogenous base remains with the silver nanoparticle composite upon its re-dispersion in one or more (c) organic solvents. The amount of such nitrogenous base(s) in the non-aqueous silver-containing dispersion is generally up to and including 10 weight %, based on the total weight of silver metal (not including any remaining reducible silver ions).

(e) Carbon Black:

In some embodiments, (e) carbon black can be incorporated into the non-aqueous silver-containing dispersions at a suitable time. Carbon black can be obtained commercially in various forms. The (e) carbon black can be added so that it is present in an amount of at least 5 weight %, based on (or relative to) the total weight of the one or more (a) polymers. Typically, the amount of (e) carbon black is at least 5 weight % and up to and including 50 weight %, or more typically in an amount of at least 5 weight % and up to and including 25 weight %, based on (or relative to) the total weight of the one or more (a) polymers.

Articles

The non-aqueous silver-containing dispersions prepared according to the present invention can be used to provide articles that can then be used in various operations or devices.

An article (or element) is typically designed to have a substrate having thereon a dry layer or dry pattern comprising a silver nanoparticle composite composition. The article has silver nanoparticles and no appreciable amounts of (b) reducible silver ions. That is, the (b) reducible ions are generally present in an amount of less than 5 mol %, based on the total amount of silver in the dry layer or dry pattern.

Thus, each article comprises a substrate (described below), and can have disposed on at least one supporting surface (or side) thereof a dry layer or dry pattern of a dry silver nanoparticle composite composition comprising:

a silver nanoparticle composite comprised of silver and one or more (a) polymers selected from one or more of cellulose acetate, cellulose acetate phthalate, cellulose acetate butyrate, cellulose acetate propionate, cellulose acetate trimellitate, hydroxypropylmethyl cellulose phthalate, methyl cellulose, ethyl cellulose, hydroxyethyl cellulose, hydroxypropylmethyl cellulose, carboxymethyl cellulose, and combinations thereof; and one or more nitrogenous bases as described above.

These silver nanoparticle composites generally have a mean particle size (d50) of at least 10 nm and up to and including 1500 nm, or of at least 20 nm and up to and including 500 nm, or even of at least 50 nm and up to and including 350 nm.

Carbon black can also be present in the dry silver nanoparticle composite composition in an amount of up to and including 50 weight %, or at least 5 weight % and up to and including 50 weight %, or even at least 5 weight % and up to and including 25 weight %, all based on (or relative to) the total weight of the one or more (a) polymers.

Such dry layers or dry patterns generally contain less than 5 mol %, or less than 2 mol %, or even less than 1 mol %, of (b) reducible silver ions, all based on the total molar amount of silver in the dry pattern or dry layer.

When one or more dry patterns of a silver nanoparticle composite composition are formed on the substrate, at least one of the patterns can comprise a combination of fine lines, each fine line having an average dry width of at least 1 μm and up to and including 20 μm, which combination of fine lines can be arranged in parallel, crossing at any desired angle, a combination thereof, or in a random arrangement. Each dry pattern can be designed to have any predetermined grid pattern that can be achieved in the art.

The presence of the (e) carbon black in the dry patterns is particularly advantageous when the substrate (described in detail below) is transparent, such as a transparent continuous polymeric film (for example a transparent continuous polycarbonate, polystyrene, or polyester film).

In many embodiments of articles, the substrate has a first supporting surface (or side) and a second opposing supporting surface (or side), and one or more dry patterns of the silver nanoparticle composite composition are disposed on the first supporting surface, and optionally, one or more dry patterns of the same or different silver nanoparticle composite composition are disposed on the second opposing supporting surface. The dry patterns can be disposed on the two opposing supporting surfaces of the substrate in any opposing arrangement, that is either directly opposite one another, or offset in some desired arrangement.

For example, in some embodiments of the article, the substrate is a transparent continuous polymeric (such as polyester) film (or web) that has a first supporting surface and a second opposing supporting surface, the article further comprising multiple (two or more) individual dry patterns formed on the first supporting surface comprise the same or different silver nanoparticle composite composition, and further comprising multiple (two or more) individual dry patterns formed on the second opposing supporting surface which opposing multiple dry patterns comprise the same or different silver nanoparticle composite composition.

For example, in such embodiments, all of the multiple individual dry patterns on both the first supporting surface and the second opposing supporting surface can comprise the same silver nanoparticle composite composition, the silver nanoparticle composite composition in each individual dry pattern comprises silver nanoparticle composite(s) having a mean particle size (d50) of at least 50 nm and up to and including 300 nm, and each of the multiple individual dry patterns comprises fine lines having an average dry width of at least 1 μm and up to and including 20 μm.

The articles described herein comprise a suitable substrate that generally has two planar surfaces: a first supporting side (or surface) and a second opposing supporting side (or surface). Such substrates can have any suitable form such as sheets of any desirable size and shape, webs of metals, films, and elongated fibers or woven fibers (such as in webs of textiles) or other porous materials, and especially continuous webs of various transparent, translucent, or opaque polymeric materials (such as polycarbonates and polyesters) that can be supplied, used, or stored as rolls. Such continuous webs or films can be used in continuous roll-to-roll manufacturing operations where the continuous web is unrolled from a supply roll and taken up using a take-up roll.

More specifically, a uniform thin film or one or more thin film patterns of a silver nanoparticle composite composition are provided in a suitable manner on one or more supporting sides of a suitable substrate to provide an article as described according to the methods described below. Typically, such articles have an initially "wet" non-aqueous silver-containing dispersion layer or pattern during and immediately after application to the substrate but the hydroxylic organic solvents can be removed as described below to provide the desired uniform thin film layer or one or more thin film patterns.

Suitable substrates can be composed of any suitable material that does not inhibit the purpose of the present invention and eventual uses of the articles. For example, substrates can be formed from materials including but are not limited to, polymeric films, metals, glasses (untreated or treated for example with tetrafluorocarbon plasma, hydrophobic fluorine, or a siloxane water-repellant material), silicon or ceramic materials such as ceramic wafers, fabrics, papers, and combinations thereof (such as laminates of various films, or laminates of papers and films) provided that a uniform thin film or thin film pattern can be formed thereon in a suitable manner and followed by thermal treatment (heating) on at least one supporting surface thereof. The substrate can be transparent, translucent, or opaque, and rigid or flexible. The substrate can include one or more auxiliary polymeric or non-polymeric layers or one or more patterns of other materials before the non-aqueous dispersion is applied according to the present invention.

More specifically, suitable substrate materials for forming precursor and product articles according to the present invention include but are not limited to, metallic films or foils, metallic films on polymer, glass, or ceramic materials, metallic films on electrically conductive film supports, semiconducting organic or inorganic films, organic or inorganic dielectric films, or laminates of two or more layers of such materials. Useful substrates can include transparent polymeric films such as poly(ethylene terephthalate) films, poly(ethylene naphthalate) films, polyimide films, polycarbonate films, polyacrylate films, polystyrene films, polyolefin films, and polyamide films, silicon and other ceramic materials, metal foils such as aluminum foils, cellulosic papers or resin-coated or glass-coated papers, glass or glass-containing composites, metals such as aluminum, tin, and copper, and metalized films. Porous fabrics, glasses, and polymeric webs can also be used.

Particularly useful substrates including continuous flexible polymeric films, metal foils, and textile webs. Useful continuous flexible polymers films include transparent continuous polymeric films such as transparent continuous polyester films such as films of poly(ethylene terephthalate), polycarbonate films, or poly(vinylidene chloride) films with or without surface-treatments or coatings as noted below.

For example, either or both supporting surfaces of the substrate can be treated with a primer layer or receptive layer, or with electrical or mechanical treatments (such as graining) to improve adhesion of the silver nanoparticle composite) composition. An adhesive layer can be thermally activated, solvent activated, or chemically activated. A separate receptive layer can have any suitable dry thickness of at least 0.05 µm when measured at 25° C.

The two supporting surfaces of the substrate, especially polymeric substrates, can be treated by exposure to corona discharge, mechanical abrasion, flame treatments, or oxygen plasmas, or coated with various polymeric films, such as poly(vinylidene chloride) or an aromatic polysiloxane.

Useful substrates can have a desired dry thickness depending upon the eventual use of the articles. For example, the substrate dry thickness (including all treatments and auxiliary layers) can be at least 0.001 mm and up to and including 10 mm, and especially for transparent polymeric films, the substrate dry thickness can be at least 0.008 mm and up to and including 0.2 mm.

The substrate used in the articles described herein can be provided in various forms, such as for example, individual sheets of any size or shape, and continuous webs such as continuous webs of transparent substrates (including transparent continuous polyester films). Such continuous webs can be divided or formed into individual first, second, and additional portions on a first supporting surface and a second opposing supporting surface on which can formed the same or different corresponding silver nanoparticle composite composition patterns in the different (or individual) portions of a supporting side (such as the first supporting sides).

Methods for Forming Silver-Containing Dispersions

Non-aqueous silver-containing dispersions according to the present invention comprising the silver nanoparticle composite described above can be provided using either of two methods (Methods I and II) according to the present invention. In both methods, the one or more (a) polymers (as described above) are mixed (or dissolved) in one or more (c) organic solvents (described above) using suitable stirring and mixing conditions.

Method I:

In a first method, one or more (d) nitrogenous base(s) (as described above) are mixed within the one or more (c) organic solvents (as described above) along with the one or more (a) polymers (as described above), to form a premix solution. This premix solution can be heated to a temperature of at least 75° C. and more likely to a temperature of at least 75° C. and up to and including 125° C. using any suitable heating means. During this heating operation, the premix solution can be continuously stirred using suitable stirring mechanism or apparatus.

While keeping this premix solution stirred at the noted temperature of at least 75° C., a solution of (b) reducible silver ions (in any silver ion-containing form as described above) in one or more (c) organic solvents (same or different from those already in premix solution) can be added to the premix solution. The rate of addition of (b) reducible silver ions can be varied, for example, by using a peristaltic pump. This addition process is generally at a rate sufficient at the noted temperature to promote the extensive reduction of the (b) reducible silver ions, for example at least 90 mol % reduction based on the original amount of (b) reducible silver ions. In general, the final amount of added (b) reducible silver ions in the premix solution is equimolar or less in relation to the (d) nitrogenous base(s) present in the premix solution. In addition, the final weight ratio of the (b) reducible silver ions to the one or more (a) polymers is at least 5:1 and up to and including 50:1, or at least 60:1 and up to and including 75:1.

The result of this addition operation is the relatively rapid formation of one or more silver nanoparticle composites in a reaction mixture.

Method II:

In a second method, (b) reducible silver ions (in any silver ion containing-form as described above) are mixed within the one or more (c) organic solvents (as described above) along with the one or more (a) polymers (as described above), to form a premix solution. This premix solution can be heated to a temperature of at least 75° C. and more likely to a temperature of at least 75° C. and up to and including 125° C. using any suitable heating means. Stirring can also be carried out during this heating operation using any suitable stirring mechanism or apparatus and in the following addition of the (d) nitrogenous base(s).

While keeping this premix at the noted temperature of at least 75° C., a solution of one or more (d) nitrogenous bases (as described above), perhaps in one or more (c) organic solvents (same or different from those already in premix solution), are added to the premix solution. This addition process is generally at a rate sufficient at the noted temperature to promote the extensive reduction of the (b) reducible silver ions, for example at least 80 mol % reduction based on the original amount of (b) reducible silver ions. In general, the final amount of added (d) nitrogenous base(s) in the premix solution is equimolar or in molar excess in relation to the (b) reducible silver ions present in the premix solution.

The result of this addition operation is the relatively rapid formation of one or more silver nanoparticle composites in a reaction mixture.

If (e) carbon black is to be included in the non-aqueous silver-containing dispersion, it can be incorporated and dispersed within at any suitable point during either Method I or Method II in appropriate amounts described above using a suitable mixing means such as a shear mixer. Suitable shear mixers are commercially available from various sources such as Silverson, Admix, and Ross.

In both Methods I and II, the resulting silver nanoparticle composite in the reaction mixture can be cooled generally to room temperature. The cooled silver nanoparticle composite can be generally isolated from the reaction mixture by either of the following two methods:

1) gravity precipitation followed by filtration of the precipitate; or 2) pouring the cooled reaction mixture into water and then filtering off the precipitate.

The isolated silver nanoparticle composite can be dried, if desired, and stored for later use. Alternatively, the silver nanoparticle composite can be immediately re-dispersed in one or more suitable (c) organic solvents (same as or different from those used above) to provide a non-aqueous silver-containing dispersion containing up to 80 weight % of silver nanoparticle composite.

Particularly useful (c) organic solvents used for this dispersing operation have a total Hansen parameter that is compatible with the total Hansen parameter of the one or more (a) polymers (such as one or more cellulosic polymers) that have been incorporated into the silver nanoparticle composite. Typically, these (c) organic solvents have a total Hansen parameter equal to or greater than the total Hansen parameter of the one or more (a) polymers (such as one or more cellulosic polymers). Thus, if a mixture of (c) organic solvents is used for dispersion, it is desirable that the total Hansen parameter of the organic solvent mixture is equal to or greater than the total Hansen parameter of the one or more (a) polymers (such as one or more cellulosic polymers) that have been incorporated within the silver nanoparticle composite.

The non-aqueous silver-containing dispersion resulting from the method described herein can be stored for later use or immediately employed in various additional operations, for example, to provide an article as described above.

For example, a non-aqueous silver-containing dispersion can be disposed onto a substrate (as described above) using any suitable equipment and method as described below, and the one or more (c) organic solvents can be removed in a suitable manner. Thus, the non-aqueous silver-containing dispersion disposed onto one or more supporting sides of a substrate to provide, upon drying, either a dry uniform film (usually thin), or one or more dry patterns of silver nanoparticle composite composition. Disposition of the non-aqueous silver-containing dispersion can be achieved in a variety of means known in the art for applying solutions or dispersions to a solid substrate.

For example, in some embodiments, a variety of films, including polymeric films composed of polyethylene, polypropylene, biaxially-oriented polypropylene, polyethylene terephthalate, polybutylene terephthalate and polyamide, can be utilized as suitable transparent substrates. The choice of substrate structure is not, however, limited to films but includes any material that can be formed into bags, shrink wrap, plates, cartons, boxes, bottles, crates, and other containers. The disposition on or application to a substrate can be carried out for example, using uniform inkjet printing, gravure printing, screen printing, flexographic printing, or by using a blade coating, gap coating, slot die coating, X-slide hopper coating, or knife on roll operations.

For example, a non-aqueous silver-containing dispersion can be disposed on the substrate (one or both supporting surfaces) in a patternwise manner using techniques described below such as flexographic printing, screen printing, gravure printing, or inkjet printing to provide one or multiple (two or more) silver nanoparticle composite composition patterns on the substrate.

For example, where the substrate has a first supporting side and a second opposing supporting side, the method according to this invention can also comprise disposing the non-aqueous silver-containing dispersion containing the silver nanoparticle composite onto the substrate in a patternwise manner to form at least one pattern (or multiple patterns) of the non-aqueous silver-containing dispersion on at least the first supporting side.

It is also possible for the method according to the present invention to be used to further dispose the same or different non-aqueous silver-containing dispersion onto the substrate in a patternwise manner to form multiple patterns of the non-aqueous silver-containing dispersion on the second opposing supporting side, or in a manner to form multiple patterns of a non-aqueous silver-containing dispersion on both the first supporting side and the second opposing supporting side using one or more flexographic printing members.

The present invention lends itself to rapid conversion of (b) reducible silver ions to electrically-conductive silver metal in an economical way so the process can be incorporated into the manufacture of various devices containing electrically-conductive silver patterns. Such operations can often be achieved using a substrate that is a continuous web that is unrolled from a supply roll and is taken up using a take-up roll, and the method is carried out in a continuous roll-to-roll manner.

More details about useful electrically-conductive silver patterns that are achievable with the present invention are now provided.

Any applied pattern of silver nanoparticle composite composition can comprise a grid of electrically-conductive fine lines (or other shapes including circles or an irregular network) as described above and the optimal dry thickness (or width) can be tailored for an intended use.

In some embodiments, the same or different silver nanoparticle composite pattern (after drying) can be provided in a suitable manner in different portions on both the first supporting side and the second opposing supporting side of the substrate to form a "duplex" or dual-sided article, and such patterns can be provided using the same or different non-aqueous silver-containing dispersion.

In many embodiments, a non-aqueous silver-containing dispersion can be applied on one or both supporting surfaces of the substrate (for example as a roll-to-roll web) using flexographic printing with one or more elastomeric relief elements such as those derived from flexographic printing plate precursors, many of which are known in the art. Some such precursors are commercially available, for example as the CYREL® Flexographic Photopolymer Plates from DuPont and the Flexcel SR and NX Flexographic plates from Eastman Kodak Company.

Useful elastomeric relief elements are derived from flexographic printing plate precursors and flexographic printing sleeve precursors, each of which can be appropriately imaged (and processed if needed) to provide the elastomeric relief elements for "printing" suitable electrically-conductive silver nanoparticle composite patterns. Useful precursors of this type are described for example, in U.S. Pat. Nos. 7,799,504 (Zwadlo et al.) and 8,142,987 (Ali et al.) and U.S. Patent Application Publication 2012/0237871 (Zwadlo), the disclosures of all of which are incorporated herein by reference. Such flexographic printing precursors can comprise elastomeric photopolymerizable layers that can be imaged through a suitable mask image to provide an elastomeric relief element (flexographic printing plate or flexographic printing sleeve). The resulting relief layer can be same or different depending upon whether the same or different patterns are to be formed on one or both supporting sides of the substrate.

In other embodiments, an elastomeric relief element can be provided from a direct (or ablation) laser-engraveable elastomeric relief element precursor, with or without integral masks, as described for example in U.S. Pat. Nos. 5,719,009 (Fan), 5,798,202 (Cushner et al.), 5,804,353 (Cushner et al.), 6,090,529 (Gelbart), 6,159,659 (Gelbart), 6,511,784 (Hiller et al.), 7,811,744 (Figov), 7,947,426 (Figov et al.), 8,114,572 (Landry-Coltrain et al.), 8,153,347 (Veres et al.), 8,187,793 (Regan et al.), and U.S. Patent Application Publications 2002/0136969 (Hiller et al.), 2003/0129530 (Leinenback et al.), 2003/0136285 (Telser et al.), 2003/0180636 (Kanga et al.), and 2012/0240802 (Landry-Coltrain et al.), the disclosures of all of which are incorporated herein by reference.

When the noted elastomeric relief elements are used to provide patterns, the non-aqueous silver-containing dispersion can be applied in a suitable manner to the uppermost relief surface (raised surface) in the elastomeric relief element. Then, application to a substrate can be accomplished in a suitable procedure while as little as possible is coated from the sides (slopes) or recesses of the relief depressions. Anilox roller systems or other roller application systems, especially low volume Anilox rollers, below 2.5 billion cubic micrometers per square inch (6.35 billion cubic micrometers per square centimeter) and associated skive knives can be used. In such embodiments, the non-aqueous silver-containing dispersion can be designed to have optimal viscosity for flexographic printing. When a substrate is moved through the roll-to-roll handling system from a flexographic printing plate cylinder to an impression cylinder, the impression cylinder applies pressure to the flexographic printing plate cylinder that transfers an image from an elastomeric relief element to the substrate.

A substrate can be "printed" one or more times using inkjet printing, gravure printing, screen printing, or flexographic printing along a web (for example, a roll-to-roll continuous web) that can contain multiple patterns (or individual precursor articles after cutting) in multiple portions of the continuous web that is passed through various stations. The same or different non-aqueous silver-containing dispersions can be applied (for example, printed) on one or both supporting sides of the substrate in the continuous roll-to-roll production operation.

After deposition of the non-aqueous silver-containing dispersion onto a substrate, for example, in a patternwise manner using flexographic printing, at least 75 weight % and up to and including 100 weight % of the (c) organi solvent(s) (described above) can be removed in any suitable manner to form an article. For example, ambient drying can be carried out in an open environment, or the article can be subject to "active" drying operations and apparatus (for example, heated drying chamber). Useful drying conditions can be as low as room temperature for as little as 5 seconds and up to and including several hours depending upon the manufacturing process. In many processes, such as roll-to-roll manufacturing operations, drying conditions can be employed at any suitable temperature, for example greater than 50° C. to remove at least 75 weight % and up to 100 weight % of all remaining organic solvents within at least 1 second and up to and including 10 seconds or even within 5 seconds.

The present invention provides at least the following embodiments and combinations thereof, but other combinations of features are considered to be within the present invention as a skilled artisan would appreciate from the teaching of this disclosure:

1. A non-aqueous silver precursor composition consisting essentially of:

(a) one or more polymers selected from one or more of cellulose acetate, cellulose acetate phthalate, cellulose acetate butyrate, cellulose acetate propionate, cellulose acetate trimellitate, hydroxypropylmethyl cellulose phthalate, methyl cellulose, ethyl cellulose, hydroxyethyl cellulose, hydroxypropylmethyl cellulose, and carboxymethyl cellulose;

(b) reducible silver ions that are present at a weight ratio to the one or more (a) polymers of at least 5:1 and up to and including 50:1;

(c) one or more organic solvents, each of which has a boiling point at atmospheric pressure of at least 100° C. and up to but less than 500° C., wherein the Hansen parameter ($\delta_T^{Polymer}$) of each of the one or more polymers is less than or equal to the Hansen parameter ($\delta_T^{Solvent}$) of each of the one or more organic solvents; and (d) a nitrogenous base having a pKa in acetonitrile of at least 15 and up to and including 25 at 25° C., the (d) nitrogenous base being present in an equimolar amount or molar excess in relation to the amount of (b) reducible silver ions.

2. The non-aqueous silver precursor composition of embodiment 1, wherein the (b) reducible silver ions are present at a weight ratio to the one or more (a) polymers of at least 5:1 and up to and including 20:1.

3. The non-aqueous silver precursor composition of embodiment 1 or 2, wherein the (b) reducible silver ions are present as a silver salt selected from the group consisting of silver nitrate, silver acetate, silver benzoate, silver nitrite, silver thiocyanate, silver myristate, silver citrate, silver phenylacetate, silver malonate, silver succinate, silver adipate, silver phosphate, silver perchlorate, silver acetylacetonate, silver lactate, silver salicylate, silver oxalate, silver 2-phenylpyridine, silver trifluoroacetate, silver fluoride or a silver fluoride complex, a β-carbonyl ketone silver (I) complex, a silver protein, a silver α-oxycarboxylate pyridine complex, and a combination thereof.

4. The non-aqueous silver precursor composition of any of embodiments 1 to 3, wherein the one or more (c) organic solvents comprises one or more hydroxylic organic solvents, each having an α-hydrogen atom and is chosen from the group consisting of ethanol, n-propanol, n-butanol, n-pentanol, n-hexanol, n-octanol, 2-ethyl-1-hexanol, n-decanol, ethylene glycol, propylene glycol, benzyl alcohol, isobutyl alcohol, isoamyl alcohol, secondary butylcarbinol, isopropyl alcohol, secondary butyl alcohol, secondary amyl alcohol, diethyl carbinol, methyl isobutyl carbinol, methyl-3-heptanol, diisobutyl carbinol, dodecanol-Z, methyl allyl carbinol, cyclohexanol, methyl cyclohexyl carbinol, phenyl methyl carbinol, 2-methoxyethanol, 2-ethoxyethanol, diethylene glycol monoethyl ether, methoxy isopropanol, and a combination thereof.

5. The non-aqueous silver precursor composition of any of embodiments 1 to 4, wherein the nitrogenous base is an aromatic cyclic compound.

6. The non-aqueous silver precursor composition of any of embodiments 1 to 5, wherein the nitrogenous base is selected from the group consisting of 1,4-diazabicyclo[2.2.2]octane (DABCO), cyclohexylamine, piperidine, N-methyl piperidine, N-methyl-3-piperidinol, ethanol amine, 2-(ethylamino)ethanol, 2-(methylamino)ethanol, 2-(butylamino)ethanol, methyldiethanolamine (MDEA), diethanolamine (DEA), diglycolamine (DGA), diethylaminoethanol (DEAE), substituted or unsubstituted non-polymeric pyridine, picolines, lutidines, quinoline, purine, isoquinoline, imidazole, benzimidazole, benzthiazole, thiazole, oxazole, benzoxazole, 4,4'-bipyridine, pyrazine, triazine, pyrimidine, nicotinic acid, isonicotinic acid, 1,8-diazabicyclo[5.4.0]undec-7-ene (DBU), and a combination thereof.

7. The non-aqueous silver precursor composition of any of embodiments 1 to 6, wherein the (a) one or more polymers is one or more of cellulose acetate, carboxymethyl cellulose, cellulose acetate butyrate, ethyl cellulose, and cellulose acetate propionate.

8. The non-aqueous silver precursor composition of any of embodiments 1 to 7, further containing (e) a carbon black.

The following Examples are provided to illustrate the practice of this invention and are not meant to be limiting in any manner.

INVENTION EXAMPLE 1

Preparation of Non-aqueous Dispersion Containing Silver Nanoparticle-Cellulose Acetate Composite using 2-Butyl Aminoethanol as the Nitrogenous Base In a 2-necked round bottomed flask a mixture of cellulose acetate (0.375 g; Aldrich, mol. wt. of 50,000, acetyl content of 39%) and 2-butyl aminoethanol (0.9 g) in 2-methoxyethanol (8 ml) was heated at 95° C. with stirring until all cellulose acetate was dissolved to form a premix solution. A solution of silver nitrate (5 g) dissolved in 2-methoxyethanol (15 ml) was slowly added to form a reaction mixture over a period of 20 minutes. During this addition, the reaction mixture became dark grey in color. It was stirred at 95° C. for another 30 minutes, cooled, and poured into methanol (500 ml). The resulting precipitate (silver nanoparticle-cellulose acetate composite) was filtered and washed with methanol to yield a gray solid (yield 98% based on theoretical silver).

Particle size distribution was measured using a dynamic light scattering method (Malvern Instruments Ltd. Zetasizer Nano-ZS (ZEN) Dynamic Light Scattering or QELS: Quasi-Elastic Light Scatter). The median silver nanoparticle composite particle diameter [Dv (50%)] was 90 nm. (see FIG. 1). The silver content of the silver nanoparticle-cellulose acetate composite was measured using thermogravimetric analysis (TGA) using a small amount of obtained gray solid that was scanned at temperatures ranging from room temperature to 700° C. in air. Organic materials are burnt and removed during the TGA scan. The residual weight at 700° C. corresponded to the amount of silver in the solid. Consistent with the starting weight ratios, the gray solid comprised 89% by weight of silver and 11% weight total of cellulose acetate and nitrogenous base.

The cooled gray-colored silver nanoparticle composite (4 g) thus obtained was added to 1-methylamino ethanol (10 ml) and re-dispersed by using a a high shear mixer (Silverson L4R) to provide a non-aqueous silver-containing dispersion containing containing the silver nanoparticle composite at 40 weight %.

A pattern of fine lines of nominal width of 7-10 μm was successfully formed from this non-aqueous silver-containing dispersion on a poly(ethylene terephthalate) film substrate using a flexographic test printer IGT F1 and flexographic printing members obtained from commercially available Kodak Flexcel NX photopolymer plates that had been imaged using a mask that was written using the Kodak Square Spot laser technology at a resolution of 12,800 dpi.

INVENTION EXAMPLE 2

Figure 2:
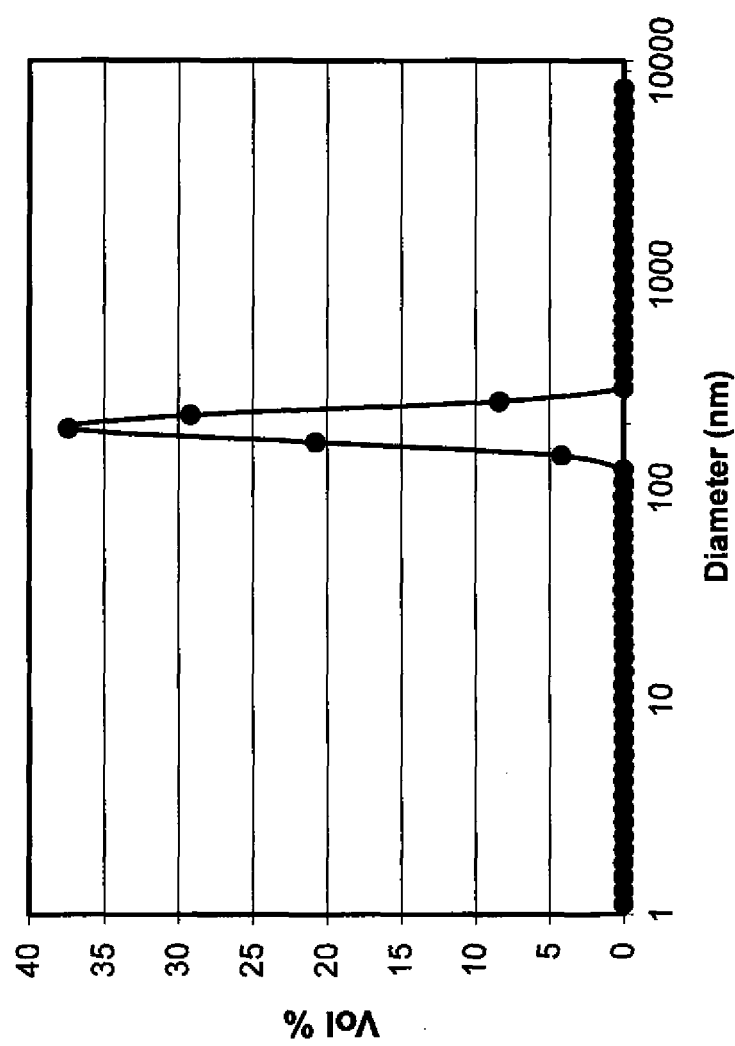
FIG. 2 is a graphical representation of particle size distribution as described below in Invention Example 2.

Preparation of Non-aqueous Dispersion Containing Silver Nanoparticle-Cellulose Acetate Propionate Composite using 2-Methyl Aminoethanol as the Nitrogenous Base In a 2-necked round bottomed flask. a mixture of cellulose acetate propionate (0.18 g; Eastman CAP 482-0.5, propionyl content 43%, Acetyl content 0.6%, mol. wt. of 25,000) and 2-methyl aminoethanol (1.5 g, mmol) in 2-methoxyethanol (7 ml) was heated at 95° C. with stirring until all cellulose acetate propionate was dissolved to form a premix solution. A solution of silver nitrate (5 g) dissolved in 2-methoxyethanol (15 ml) was added to the premix solution over a period of 35 minutes. The resulting reaction mixture was stirred at 95° C. for another 45 minutes, cooled, and poured into water (400 ml). The resulting precipitate was filtered and washed with methanol. A grey colored solid was obtained (yield of 97% based on silver). Particle size distribution was measured using a dynamic light scattering method (Malvern Instruments Ltd. Zetasizer Nano-ZS (ZEN) Dynamic Light Scattering or QELS: Quasi-Elastic Light Scatter). The median particle diameter [Dv (50%)] was 340 nm determined. (see FIG. 2).

Figure 3:
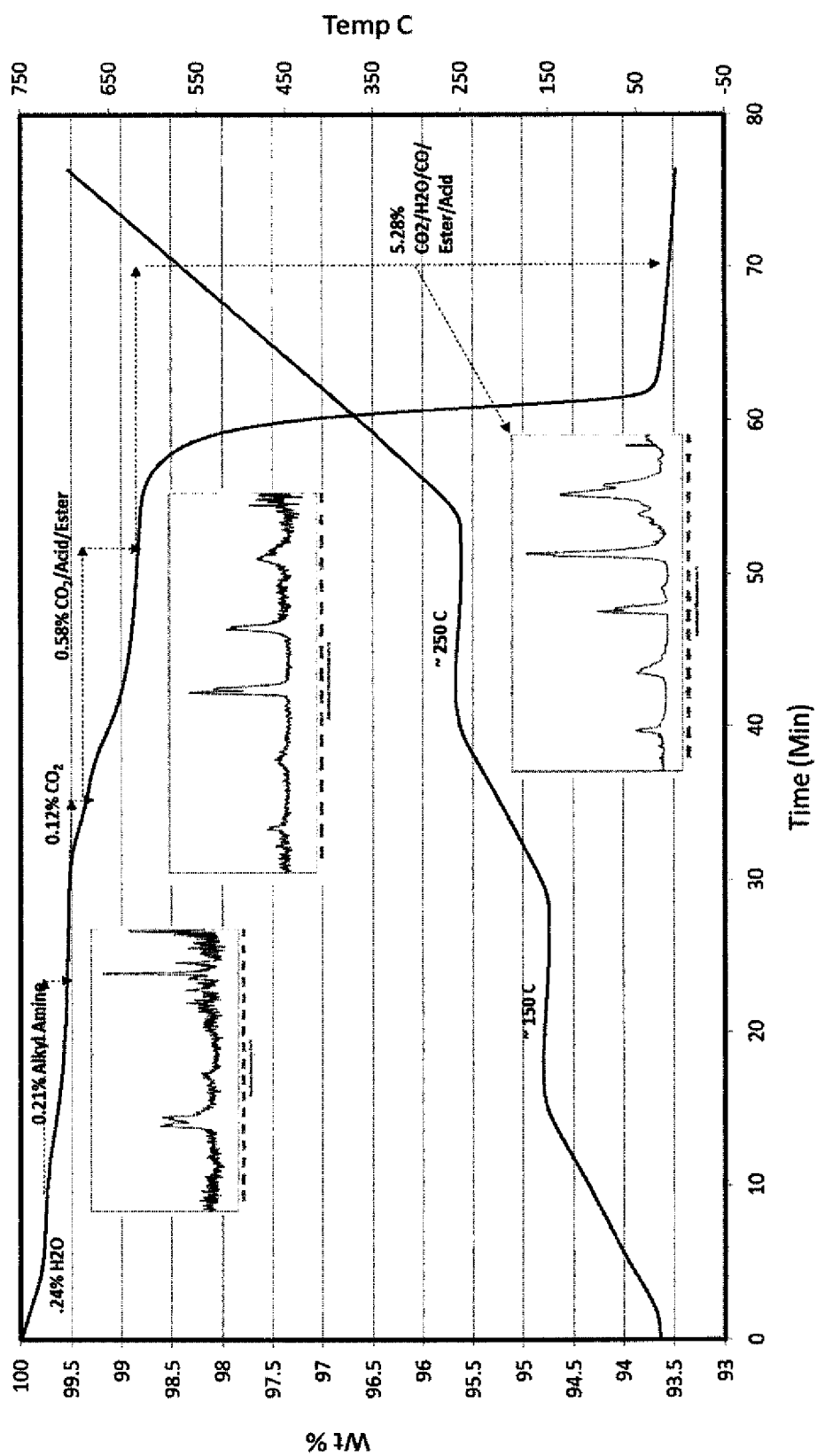
FIG. 3 is a graphical representation of chemical analysis of the silver nanoparticles-cellulose polymer composite prepared in Invention Example 2 below.

Chemical analysis of the resulting solid was carried out by TGA-FTIR (Thermo Gravimetric Analysis-Forier Transform Infrared) on a 95.1 mg sample over the temperature range of room temperature to 700° C., using a ramp protocol of 10 degrees/minute to 150° C. (isotherm 15 minutes), 10 degrees/minute to 250° C. (isotherm 15 minutes), and 20 degrees/minute to 700° C. A purge of $N_2$ gas, at a rate of 10 $cm^3$/minute was used to sweep the evolved gases through the transfer line and the infrared (IR) gas cell, both heated at a constant temperature of 240° C. Sixteen IR spectra (interferograms) of the evolved gases, at 4 cm−1 resolution, were co-added at approximately 10 second intervals. A TE-TGS detector was used for IR detection. The data showed an initial weight loss of about 0.24% due to water as the sample was initially heated. From about 105° C. into the isotherm at 150° C., a weight loss of 0.21% is seen due to the nitrogenous base. As the dispersion was heated to 250° C., a weight loss of about 0.7% was seen due to carbon dioxide and propionic acid, possibly mixed with an ester. A major weight loss of >5% was seen above 250° C. due to a mixture of carbon dioxide, carbon monoxide, water, and what is likely cellulose acetate propionate. Overall, the resulting solid (silver nanoparticle composite) was determined to contain 94.7% by weight of silver, about 0.3% by weight of the nitrogenous base and 5% by weight cellulose acetate propionate (see FIG. 3).

INVENTION EXAMPLE 3

Figure 4:
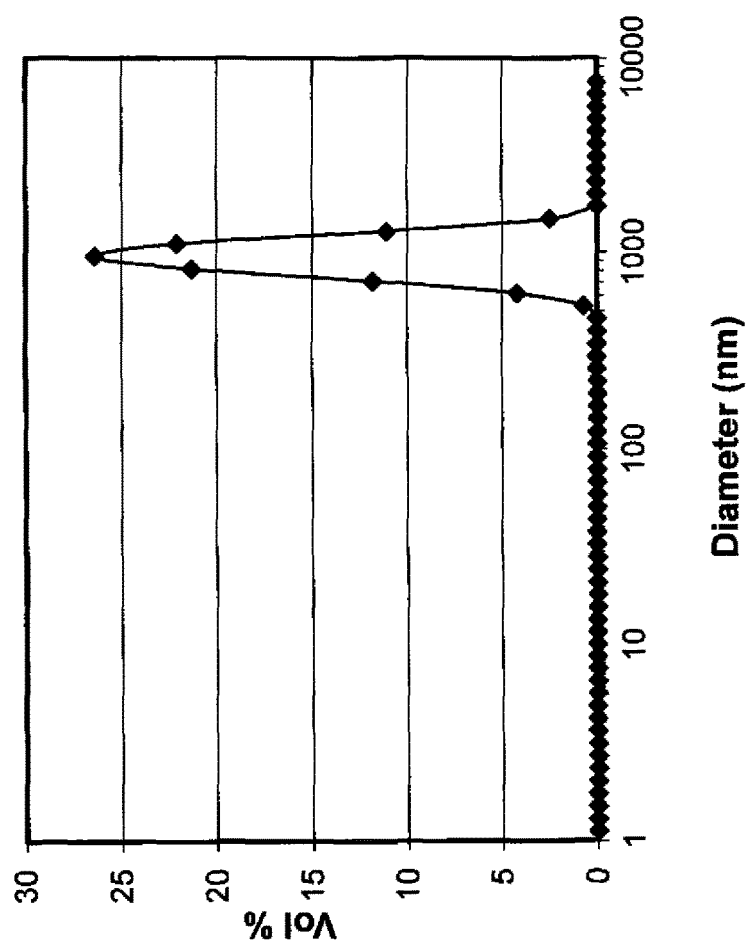
FIG. 4 is a graphical representation of particle size distribution as described below in Invention Example 3.

Preparation of Non-Aqueous Dispersion of Silver Nanoparticle-Cellulose Acetate Propionate Composite Using 1,8-Diazabicyclo[5.4.0]undec-7-ene as the Nitrogenous Base In a 2-necked round bottomed flask, a mixture of cellulose acetate propionate (0.4 g; Eastman CAP 482-20, propionyl content 48%, Acetyl content 1.3%, Mol. wt. of 75,000) and 1,8-diazabicyclo[5.4.0]undec-7-ene (16 g, mmol) in 2-methoxyethanol (28 ml) was heated at 95° C. with stirring until all cellulose acetate propionate was dissolved to form a premix solution. A solution of silver nitrate (8.8 g) dissolved in 2-methoxyethanol (100 ml) was added to the premix solution over a period of 80 minutes. The resulting reaction mixture was stirred at 95° C. for another 20 minutes, cooled, and poured into water (800 ml). The resulting precipitate was filtered and washed with methanol. A grey colored solid was obtained (yield of 98% based on silver). Particle size distribution was measured a dynamic light scattering method (Malvern Instruments Ltd. Zetasizer Nano-ZS (ZEN) Dynamic Light Scattering or QELS: Quasi-Elastic Light Scatter). The median particle diameter [Dv (50%)] was determined to be 350 nm. (see FIG. 4).

The gray colored silver nanoparticle composite (6 g) thus obtained was added to 1-methoxy-2-propanol (10 ml) and re-dispersed using a a high shear mixer (Silverson L4R) to obtain a non-aqueous silver-containing dispersion containing 60 weight % silver nanoparticle composite.

A pattern of lines of nominal width of 2-20 mm was successfully formed from this non-aqueous silver-containing dispersion on a poly(ethylene terephthalate) film substrate using a flexographic test printer IGT F1 and flexographic printing members obtained from commercially available Kodak Flexcel NX photopolymer plates that had been imaged using a mask that was written using the Kodak Square Spot laser technology at a resolution of 12,800 dpi.

INVENTION EXAMPLE 4

Preparation of Non-Aqueous Dispersion of Silver Nanoparticle-Cellulose Acetate Propionate Composite Using 4-Methylpyridine as the Nitrogeous Base In a 2-necked round bottomed flask, a mixture of cellulose acetate propionate (0.375 g; Aldrich, Mol. wt. of 50,000, Acetyl content 39%) and 2-methoxyethanol (7 ml) was heated at 85° C. with stirring until all cellulose acetate propionate was dissolved. A solution of silver nitrate (5 g) dissolved in 2-methoxyethanol (15 ml) was added into the reaction vessel and the resulting premix solution was stirred while being heated at 85° C. The nitrogenous base 4-methylpyridine (1.5 g, mmol) was added in portions and heating was continued of the resulting reaction mixture that slowly turned yellow and then brown in color. Reaction was continued under heating at 85° C. for 20 hours and then the the heated reaction mixture was poured into methanol (100 ml). The resulting precipitate was filtered and washed with methanol to provide a grey-colored solid (yield 97% based on silver).

Particle size distribution was measured using a dynamic light scattering method (Malvern Instruments Ltd. Zetasizer Nano-ZS (ZEN) Dynamic Light Scattering or QELS: Quasi-Elastic Light Scatter). A median particle diameter [Dv (50%)] was determined to be 270 nm.

INVENTION EXAMPLE 5

Preparation of Non-Aqueous Dispersion of Silver Nanoparticle-Cellulose Acetate Propionate Composite Using Silver Acetate In a two-necked round bottomed flask, cellulose acetate propionate (0.36 g, mol. wt. of 15,000) was dissolved in 1-methoxy-2-propanol (19.0 g) with stirring at 95° C. Silver acetate (11.0 g) was then added to the flask to form a slurry or premix solution. A solution of 2-(methylamino)ethanol (3.0 g) in 1-methoxy -2-propanol (4.5 ml) was quickly added to the premix solution and heating was continued for another sixty minutes. The resulting grey color slurry was poured into 300 ml of water and the resulting precipitate was filtered and dried.

Particle size distribution was measured using a dynamic light scattering method (Malvern Instruments Ltd. Zetasizer Nano-ZS (ZEN) Dynamic Light Scattering or QELS: Quasi-Elastic Light Scatter). A median particle diameter [Dv (50%)] was determined to be 770 nm.

INVENTION EXAMPLE 6

Preparation of Non-Aqueous Dispersion of Silver Nanoparticle-Ethyl Cellulose Composite In a two-necked round bottomed flask, ethyl cellulose [0.42 g, Scientific Polymer Products Cat#463 ethyl cellulose (10 cps), ethoxyl content 48%] was dissolved in 2-methoxyethanol (36.24 g) by stirring at 80° C. for 30 minutes. 2-Methylamino ethanol (7.79 grams) was added to the solution as a nitrogenous base to form a premix solution. A solution of silver nitrate in 2-methoxyethanol (105 g, 8 weight % silver salt) was then added to the premix solution over two hours. Heating and stirring were continued for another thirty minutes. The resulting slurry was poured into 800 ml water to form a precipitate that was filtered and dried.

ZEN Particle Sizing of another aliquot of the premix solution prior to precipitation determined a silver nanoparticle composite particle size distribution having a mean size of 1200 nm. The resulting precipitate was re-dispersed in 1-methoxy-2-propanol (50% solids) using a a high shear mixer (Silverson L4R) to obtain a printable non-aqueous silver-containing dispersion.

Preparation of Non-Aqueous Dispersion of Silver Nanoparticle-Cellulose Acetate Propionate Composite Using Silver α-hydroxyisobutyrate (No Precipitation Carried Out)

In a 50 ml round bottom flask, cellulose acetate propionate (0.104 g, Eastman CAP-482-20) was dissolved in 1-methoxy-2-propanol (4.0 g) and silver α-hydroxyisobutyrate (4.0 g, 18.96 mmol) was then added to create a slurry. The slurry was heated at 118° C. using an oil bath and while stirring, 2-(methylamino)ethanol (1.42 g, 18.96 mmol) nitrogenous base was added quickly and heated for an additional 90 minutes. The formed dispersion was removed from heat and cooled to room temperature. The particle size distribution was measured using a dynamic light scattering method (Malvern Instruments Ltd. Zetasizer Nano-ZS (ZEN) Dynamic Light Scattering or QELS: Quasi-Elastic Light Scatter). A median particle diameter [Dv (50%)] was determined to be 377 nm.

A non-aqueous silver-containing dispersion was formed having 25 weight % silver nanoparticle composites (Ag: cellulose polymer of 95:5) re-dispersed in 3:1 1-methoxy-2-propanol-2-(methylamino) ethanol solvent mixture, and was used as is for flexographic printing as described in the previous Examples.

The invention has been described in detail with particular reference to certain preferred embodiments thereof, but it will be understood that variations and modifications can be effected within the spirit and scope of the invention.

The invention claimed is:

1. A non-aqueous silver precursor composition consisting essentially of:
   (a) one or more polymers selected from one or more of cellulose acetate, cellulose acetate phthalate, cellulose acetate butyrate, cellulose acetate propionate, cellulose acetate trimellitate, hydroxypropylmethyl cellulose phthalate, methyl cellulose, ethyl cellulose, hydroxyethyl cellulose, hydroxypropylmethyl cellulose, and carboxymethyl cellulose;
   (b) reducible silver ions that are present at a weight ratio to the one or more (a) polymers of at least 5:1 and up to and including 50:1;
   (c) one or more organic solvents, each of which has a boiling point at atmospheric pressure of at least 100° C. and up to but less than 500° C.,wherein the Hansen parameter ($\delta_T^{Polymer}$) of each of the one or more polymers is less than or equal to the Hansen parameter ($\delta_T^{Solvent}$) of each of the one or more organic solvents; and
   (d) a nitrogenous base having a pKa in acetonitrile of at least 15 and up to and including 25 at 25° C., the (d) nitrogenous base being present in an equimolar amount or molar excess in relation to the amount of (b) reducible silver ions.

2. The non-aqueous silver precursor composition of claim 1, wherein the (b) reducible silver ions are present at a weight ratio to the one or more (a) polymers of at least 5:1 and up to and including 20:1.

3. The non-aqueous silver precursor composition of claim 1, wherein the (b) reducible silver ions are present as a silver salt selected from the group consisting of silver nitrate, silver acetate, silver benzoate, silver nitrite, silver thiocyanate, silver myristate, silver citrate, silver phenylacetate, silver malonate, silver succinate, silver adipate, silver phosphate, silver perchlorate, silver acetylacetonate, silver lactate, silver salicylate, silver oxalate, silver 2-phenylpyridine, silver trifluoroacetate, silver fluoride or a silver fluoride complex, a β-carbonyl ketone silver (I) complex, a silver protein, a silver α-oxycarboxylate pyridine complex, and a combination thereof.

4. The non-aqueous silver precursor composition of claim 1, wherein the one or more (c) organic solvents comprises one or more hydroxylic organic solvents, each having an α-hydrogen atom and is chosen from the group consisting of ethanol, n-propanol, n-butanol, n-pentanol, n-hexanol, n-octanol, 2-ethyl-1-hexanol, n-decanol, ethylene glycol, propylene glycol, benzyl alcohol, isobutyl alcohol, isoamyl alcohol, secondary butylcarbinol, isopropyl alcohol, secondary butyl alcohol, secondary amyl alcohol, diethyl carbinol, methyl isobutyl carbinol, methyl-3-heptanol, diisobutyl carbinol, dodecanol-Z, methyl allyl carbinol, cyclohexanol, methyl cyclohexyl carbinol, phenyl methyl carbinol, 2-methoxyethanol, 2-ethoxyethanol, diethylene glycol monoethyl ether, methoxy isopropanol, and a combination thereof.

5. The non-aqueous silver precursor composition of claim 1, wherein the nitrogenous base is an aromatic cyclic compound.

6. The non-aqueous silver precursor composition of claim 1, wherein the nitrogenous base is selected from the group consisting of 1,4-diazabicyclo [2.2.2]octane (DABCO), cyclohexylamine, piperidine, N-methyl piperidine, N-methyl-3-piperidinol, ethanol amine, 2-(ethylamino)ethanol, 2-(methylamino)ethanol, 2-(butylamino)ethanol, methyldiethanolamine (MDEA), diethanolamine (DEA), diglycolamine (DGA), diethylaminoethanol (DEAE), substituted or unsubstituted non-polymeric pyridine, picolines, lutidines, quinoline, purine, isoquinoline, imidazole, benzimidazole, benzthiazole, thiazole, oxazole, benzoxazole, 4,4'-bipyridine, pyrazine, triazine, pyrimidine, nicotinic acid, and isonicotinic acid, 1,8-diazabicyclo[5.4.0]undec-7-ene (DBU), and a combination thereof.

7. The non-aqueous silver precursor composition of claim 1, wherein the (a) one or more polymers is one or more of cellulose acetate, carboxymethyl cellulose, cellulose acetate butyrate, ethyl cellulose, and cellulose acetate propionate.

* * * * *